US012564188B2

(12) United States Patent
Sevenler et al.

(10) Patent No.: US 12,564,188 B2
(45) Date of Patent: Mar. 3, 2026

(54) HYDROGEL BEADS FOR CONTROLLED UPTAKE AND RELEASE OF CRYOPROTECTIVE AGENTS

(71) Applicant: The General Hospital Corporation, Boston, MA (US)

(72) Inventors: Derin Sevenler, Cambridge, MA (US); Rebecca Sandlin, Melrose, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 447 days.

(21) Appl. No.: 18/016,101

(22) PCT Filed: Jul. 19, 2021

(86) PCT No.: PCT/US2021/042204
§ 371 (c)(1),
(2) Date: Jan. 13, 2023

(87) PCT Pub. No.: WO2022/016148
PCT Pub. Date: Jan. 20, 2022

(65) Prior Publication Data
US 2023/0270103 A1 Aug. 31, 2023

Related U.S. Application Data

(60) Provisional application No. 63/053,135, filed on Jul. 17, 2020.

(51) Int. Cl.
*A01N 1/162* (2025.01)
*A01N 1/125* (2025.01)
*C12N 5/0783* (2010.01)

(52) U.S. Cl.
CPC ............. *A01N 1/162* (2025.01); *A01N 1/125* (2025.01); *C12N 5/0636* (2013.01); *C12N 2533/74* (2013.01); *C12N 2537/10* (2013.01)

(58) Field of Classification Search
CPC ................................ A01N 1/162; A01N 1/125
See application file for complete search history.

(56) References Cited

U.S. PATENT DOCUMENTS

| | | | |
|---|---|---|---|
| 2008/0020049 A1* | 1/2008 | Darling ................. | C12N 5/0075 435/325 |
| 2009/0130756 A1 | 5/2009 | Klann et al. | |
| 2015/0087056 A1 | 3/2015 | Pelle Meddahi et al. | |
| 2020/0040094 A1* | 2/2020 | Liu ..................... | C07K 16/2896 |
| 2020/0056223 A1* | 2/2020 | Bell ..................... | C12Q 1/6806 |

FOREIGN PATENT DOCUMENTS

| | | |
|---|---|---|
| WO | WO 2011/089391 | 7/2011 |
| WO | WO 2018/005802 | 1/2018 |

OTHER PUBLICATIONS

McNeil PL and Warder E. Glass Beads Load Macromolecules Into Living Cells. J Cell Sci. 88: 669-678. (Year: 1987).*
Cialek CA et al. Bead Loading Proteins and Nucleic Acids into Adherent Human Cells. J. Vis. Exp. (172), e62559, doi:10.3791/62559. (Year: 2021).*
Beres and Drobyski, "The Role of Regulatory T Cells in the Biology of Graft Versus Host Disease," Front Immunol, Jun. 2013, 4:163, 9 pages.
Best, "Cryoprotectant Toxicity: Facts, Issues, and Questions," Rejuvenation Res, Oct. 2015, 18(5):422-36.
Calmels et al., "Preclinical evaluation of an automated closed fluid management device: Cytomate TM , for washing out DMSO from hematopoietic stem cell grafts after thawing," Bone Marrow Transplantation, May 2003, 31(9):823-8.
Chen et al., "Synthesis of Nonspherical Microcapsules through Controlled Polyelectrolyte Coating of Hydrogel Templates," Langmuir, 2015; 31(33):9228-35, 9 pages.
Cheng et al., "Cold-Responsive Nanocapsules Enable the Sole-Cryoprotectant-Trehalose Cryopreservation of β Cell-Laden Hydrogels for Diabetes Treatment," Nano-Micro Small, Dec. 2019, 15(50):1904290, 9 pages.
Costantini et al., "Effects of cryopreservation on lymphocyte immunophenotype and function," Journal of Immunological Methods, Jul. 2003, 278(1-2):145-55.
Cox et al., "Historical perspectives and the future of adverse reactions associated with haemopoietic stem cells cryopreserved with dimethyl sulfoxide," Cell Tissue Bank, Jun. 2012, 13(2):203-15.
Diaz-Dussan et al., "Trehalose-based Polyethers for Cryopreservation and 3D Cell Scaffolds," Biomacromolecules, Mar. 2020, 21(3):1264-1273, 29 pages.
Esensten et al., "Engineering Therapeutic T Cells: From Synthetic Biology to Clinical Trials," Annual Review of Pathology, Jan. 2017, 12:305-30.
Fesnak et al., "Engineered T cells: the promise and challenges of cancer immunotherapy," Nature Reviews Cancer, Aug. 2016, 16(9):566-81.
Golab et al., "Challenges in cryopreservation of regulatory T cells (Tregs) for clinical therapeutic applications," International Immunopharmacology, Jul. 2013, 16(3):371-5.
Heo et al., "Controlled loading of cryoprotectants (CPAs) to oocyte with linear and complex CPA profiles on a microfluidic platform," Lab Chip, Oct. 2011, 11(20):3530-7.

(Continued)

*Primary Examiner* — Lora E Barnhart Driscoll
(74) *Attorney, Agent, or Firm* — Fish & Richardson P.C.

(57) ABSTRACT

Hydrogel beads having tunable rates of loading and unloading of cryoprotective agents are provided herein. Such hydrogel beads can be dispersed throughout a cell suspension to enable loading and unloading of cryoprotective agents from cells in a gradual and distributed manner that protects the cells from osmotic damage. Lymphocyte viability after cryopreservation is significantly greater when cryoprotective agents are loaded and unloaded using hydrogel beads compared to conventional media exchange methods.

18 Claims, 11 Drawing Sheets

(56) References Cited

OTHER PUBLICATIONS

Hopewell et al., "Tumor-infiltrating lymphocytes: Streamlining a complex manufacturing process," Cytotherapy, Mar. 2019, 21(3):307-14, 8 pages.

International Preliminary Report on Patentability in International Appln. No. PCT/US2021/042204, mailed on Jan. 26, 2023, 9 pages.

International Search Report and Written Opinion in International Appln. No. PCT/US2021/042204, mailed on Dec. 30, 2021, 12 pages.

Künkele et al., "Preclinical Assessment of CD171-Directed CART-cell Adoptive Therapy for Childhood Neuroblastoma: CE7 Epitope Target Safety and Product Manufacturing Feasibility," Clin Cancer Res, Jan. 2017, 23(2):466-77.

Kvarnström et al., "Effect of cryopreservation on expression of Th1 and Th2 cytokines in blood mononuclear cells from patients with different cytokine profiles, analysed with three common assays: an overall decrease of interleukin-4," Cryobiology, Oct. 2004, 49(2):157-68.

Levine et al., Global Manufacturing of CAR T Cell Therapy, Molecular Therapy-Methods & Clinical Development, Dec. 2016, 4:92-101.

Mock et al., "Automated Lentiviral Transduction of T Cells with Cars Using the Clinimacs Prodigy," Blood, Dec. 2015, 126(23):2043, 6 pages.

Neelapu et al., "Axicabtagene Ciloleucel CAR T-Cell Therapy in Refractory Large B-Cell Lymphoma," New England Journal of Medicine, Dec. 2017, 377(26):2531-44.

Notman et al., "Molecular Basis for Dimethylsulfoxide (DMSO) Action on Lipid Membranes," J Am Chem Soc, Nov. 2006, 128(43):13982-3.

Papadopoulou et al., "Activity of Broad-Spectrum T Cells as Treatment for AdV, EBV, CMV, BKV, and HHV6 Infections after HSCT," Science Translational Medicine, Jun. 2014, 6(242):242ra83, 12 pages.

Pi et al., "Characterizing the "sweet spot" for the preservation of a T-cell line using osmolytes," Scientific Reports, Nov. 2018, 8(1):16223, 13 pages.

Roberts et al., "Axicabtagene ciloleucel, a first-in-class CAR T cell therapy for aggressive NHL," Leukemia & Lymphoma, 2018, 59(8):1785-96.

Rosenberg et al., "Adoptive cell transfer: a clinical path to effective cancer immunotherapy," Nature Reviews Cancer, Apr. 2008, 8(4):299-308.

Sarnaik et al., "Abstract 136: Safety and efficacy of cryopreserved autologous tumor infiltrating lymphocyte therapy (LN-144, lifileucel) in advanced metastatic melanoma patients who progressed on multiple prior therapies including anti-PD-1," Abstract, Presented at Proceedings of the ASCO-SITC Annual Meeting, Feb. 28-Mar. 2, 2019, San Francisco, CA; JCO, May 2019, 37(Suppl 15):2518-2518, 1 page.

Schuster et al., "Chimeric Antigen Receptor T-Cells in Refractory B-Cell Lymphomas," New England Journal of Medicine, Dec. 2017, 377:2545-54.

Shu et al., "A study of the osmotic characteristics, water permeability, and cryoprotectant permeability of human vaginal immune cells," Cryobiology, Apr. 2016, 72(2):93-9.

Stevanović et al., "Complete Regression of Metastatic Cervical Cancer After Treatment With Human Papillomavirus-Targeted Tumor-Infiltrating T Cells," J Clin Oncol, May 2015, 33(14):1543-50, 10 pages.

Weng et al., "A highly-occupied, single-cell trapping microarray for determination of cell membrane permeability," Lab on a Chip, Nov. 2017, 17(23):4077-88.

Zhang and Peppas, "Synthesis and Characterization of pH- and Temperature-Sensitive Poly(methacrylic acid)/Poly(N-isopropylacrylamide) Interpenetrating Polymeric Networks," Macromolecules, 2000, 33:102-7.

Zhang et al., "The encapsulation and intracellular delivery of trehalose using a thermally responsive nanocapsule," Nanotechnology, Jul. 2009, 20(27):275101, 14 pages.

Zhao et al., "The Future of Layer-by-Layer Assembly: A Tribute to ACS Nano Associate Editor Helmuth Möhwald," ACS Nano, Jun. 2019, 13(6):6151-69, 19 pages.

Zilionis et al., "Single-cell barcoding and sequencing using droplet microfluidics," Nature Protocols, Jan. 2017, 12(1):44-73.

Bunker et al., "Switchable Hydrophobic-Hydrophilic Surfaces," San Report, SAND2002-3870, approved for public release and published by Sandia National Laboratories (Albuquerque, NM and Livermore, CA), with unlimited dissemination, Dec. 2002, retrievable from URL <https://www.osti.gov/servlets/purl/806703/>, 38 pages.

Sevenler et al., "Abstract S50: Programmable uptake and release of cryoprotective agents from semipermeable hydrogel beads," Presented at Proceedings of the CRYO2020 Virtual Meeting, Jul. 21-23, 2020; and published in Cryobiology, vol. 97:254-305, at p. 266, Dec. 2020.

* cited by examiner

Gradual CPA Release: 5 uL uncoated beads

HYDROGEL BEADS FOR CONTROLLED UPTAKE AND RELEASE OF CRYOPROTECTIVE AGENTS

CLAIM OF PRIORITY

This application is a U.S. National Phase Application under 35 U.S.C. § 371 of International Patent Application No. PCT/US2021/042204, filed on Jul. 19, 2021, which claims the benefit of U.S. Provisional Patent Application No. 63/053,135, filed on Jul. 17, 2020, which is incorporated by reference herein in its entirety.

FEDERALLY SPONSORED RESEARCH OR DEVELOPMENT

This invention was made with government support under Grant No. DK114506 awarded by the National Institutes of Health. The government has certain rights in the invention.

FIELD

The subject matter disclosed herein generally relates to methods and compositions for cryopreservation of cells, e.g., white blood cells, such as lymphocytes (e.g., T cells).

BACKGROUND

Cell-penetrating cryoprotective agents (CPAs) are required to inhibit or prevent the formation of intracellular ice during cryopreservation by slow cooling of mammalian cell suspensions. Common cryopreservation medium formulations use high volume fractions (e.g., >10%) of miscible solvents such as dimethyl sulfoxide (DMSO) or glycerol, which diffuse across lipid bilayer membranes. However, the plasma membranes of most cells are much less permeable to these CPAs than they are to water, due to the presence of water-specific aquaporins. Care must therefore be taken to prevent excessive hypertonic and hypotonic shock when washing cell suspensions into and out of such cryo-media, respectively.

Gradual dropwise addition of concentrated CPAs is commonly used to try to reduce hypertonic shock during CPA loading. Likewise, gradual dropwise dilution with isotonic medium is standard practice for washing thawed cells. Unfortunately, these practices are not easily scaled to clinical applications (e.g., cell therapies) that require larger sample volumes (e.g., ~100 mL, ~1.0×10⁹ cells), because higher shear rates required to achieve the same mixing length scale for larger volumes in the same period of time can be damaging to cells. The growing number of new clinical applications for precious patient-derived and/or engineered therapeutic cells underscores the need for methods and materials to mediate the gradual exchange of CPAs in large volume cell suspensions.

SUMMARY OF THE INVENTION

The present disclosure is based, at least in part, on the surprising discovery that hydrogel beads can act as molecular "sponges" that release and/or absorb cryoprotective agents from a suspension of cells, e.g., animal cells, such as white blood cells, e.g., lymphocytes, in a gradual and distributed manner that protects the cells from osmotic damage. It was also demonstrated that unloading of cryoprotective agents from lymphocytes thawed after cryopreservation using hydrogel beads resulted in substantially more viable lymphocytes than conventional media exchange methods.

Accordingly, aspects of the present disclosure provide hydrogel beads including one or more cryoprotective agents. In some embodiments, the hydrogel beads have a diameter of 1 to 5 mm. In some embodiments, the hydrogel bead has a volume of 0.5 to 65 μL. In some embodiments, the hydrogel beads have a weight of 0.5 to 65 mg.

In some embodiments, the one or more cryoprotective agents are present in the hydrogel bead at an amount of 2.5% to 50% (v/v). In some embodiments, the one or more cryoprotective agents include an intracellular cryoprotective agent, an extracellular cryoprotective agent, or both. In some embodiments, the intracellular cryoprotective is selected from the group consisting of glycerol, ethylene glycol, 1,2-propanediol, and dimethyl sulfoxide (DMSO). In some embodiments, the extracellular cryoprotective agent is selected from the group consisting of sugars, dextran, polyvinyl pyrrolidone, and hydroxyethyl starch.

In some embodiments, the hydrogel bead includes or consists of a biological polymer, a synthetic polymer, or a combination thereof. In some embodiments, the biological polymer comprises dextran, chitosan, alginate, fibrin, collagen, gelatin, or a combination thereof. In some embodiments, the synthetic polymer comprises poly(hydroxyethyl methacrylate) (PHEMA), poly(vinyl alcohol) (PVA), poly(ethylene glycol) (PEG), poly(acrylic acid) (PAA), poly(methacrylic acid) (PMMA), and polyacrylamide (PAA).

Aspects of the present disclosure provide compositions including any of the hydrogel beads described herein. In some embodiments, the compositions further comprise a solution comprising one or more cryoprotective agents. In some embodiments, the compositions further comprise a preservative.

Aspects of the present disclosure provide methods of preparing a plurality of hydrogel beads including one or more cryoprotective agents, the methods including (a) incubating a plurality of hydrogel beads, as described herein, and a cryoprotective solution including one or more cryoprotective agents for a time and under sufficient conditions for uptake of the one or more cryoprotective agents by the plurality of hydrogel beads, wherein each hydrogel bead in the plurality of hydrogel beads is set forth as described herein, and (b) separating the plurality of hydrogel beads from the cryoprotective solution.

In some embodiments, after step (a), the one or more cryoprotective agents are present in the hydrogel beads in a concentration of about 2.5 to 50% (v/v). In some embodiments, the concentration of the one or more cryoprotective agents in the cryoprotective solution is 2.5% to 50% (v/v).

In some embodiments, the volume of the cryoprotective solution is 5 to 20 times greater than the volume of the plurality of hydrogel beads.

In some embodiments, the plurality of hydrogel beads and the cryoprotective solution are incubated at room temperature. In some embodiments, the plurality of hydrogel beads and the cryoprotective solution are incubated for 1 to 60 minutes. In some embodiments, the plurality of hydrogel beads and the cryoprotective solution are incubated with mixing. In some embodiments, the plurality of hydrogel beads is separated from the cryoprotective solution using aspiration, filtration, centrifugation, or a combination thereof.

In some embodiments, the methods further include storing the plurality of hydrogel beads in a sterile airtight container.

In some embodiments, the methods further include synthesizing the plurality of hydrogel beads prior to step (a). In some embodiments, the plurality of hydrogel beads are obtained from commercially available sources.

Aspects of the present disclosure provide methods for cryopreservation of cells, the, including (a) suspending the cells in an isotonic solution, (b) adding a plurality of hydrogel beads comprising one or more cryoprotective agents to the isotonic solution, wherein each hydrogel bead in the plurality of hydrogel beads is set forth as described herein, (c) incubating the isotonic solution and the plurality of hydrogel beads for a time and under conditions sufficient to release the one or more cryoprotective agents from the plurality of hydrogel bead into the isotonic solution, (d) separating the cells from the plurality of hydrogel beads, and (e) cooling the cells to a temperature sufficient to cryopreserve the cells.

In some embodiments, the isotonic solution is phosphate buffered saline (PBS) or cell culture media.

In some embodiments, the cells are animal cells, bacterial cells, plant cells, or fungal cells. In some embodiments, the animal cells are mammalian cells, e.g., human cells. In some embodiments, the mammalian cells are white blood cells. In some embodiments, the white blood cells are granulocytes, monocytes, lymphocytes, or combinations thereof. In some embodiments, the granulocytes are neutrophils, eosinophils, basophils, or combinations thereof. In some embodiments, the lymphocytes are T cells, B cells, natural killer (NK) cells, or combinations thereof.

As used herein, the term "cells" refers to any cells suitable for cryopreservation including, but not limited to, animal cells (e.g., mammalian cells such as human cells), plant cells, bacterial cells, and fungal cells. A heterogeneous suspension of cells or a homogenous suspension of cells can be cryopreserved as described herein.

In some embodiments, in step (b) of the method described above, the amount of the isotonic solution by volume is 2 to 4 times greater than the amount of the plurality of hydrogel beads by weight.

In some embodiments, in step (c) of the method described above, the cells, e.g., lymphocytes, and the plurality of hydrogel beads are incubated at room temperature. In some embodiments, in step (c), the cells and the plurality of hydrogel beads are incubated for 1 to 20 minutes. In some embodiments, in step (c), the cells and the plurality of hydrogel beads are incubated with mixing.

In some embodiments, in step (d), separating the cells from the plurality of hydrogel beads comprises aspiration, filtration, centrifugation, or a combination thereof.

In some embodiments, the temperature sufficient to cryopreserve the cells, such as lymphocytes, is −80° C. or a temperature below −80° C.

Aspects of the present disclosure provide methods for recovering cryopreserved cells in a cryopreservation solution comprising one or more cryoprotective agents, the methods including (a) thawing the cryopreserved cells in the cryopreservation solution at a temperature above freezing, (b) adding a plurality of hydrogel beads to the cryopreservation solution, wherein each hydrogel bead in the plurality of hydrogel beads is set forth as described herein, (c) incubating the plurality of hydrogel beads and the cryopreservation solution for a time and under conditions sufficient for the plurality of hydrogel beads to absorb the one or more cryoprotective agents, and (d) separating the thawed cells from the plurality of hydrogel beads.

In some embodiments, the cryopreserved cells are cryopreserved plant cells, cryopreserved animal cells, cryopreserved bacterial cells, or cryopreserved fungal cells. In some embodiments, the cryopreserved animal cells are cryopreserved mammalian cells. In some embodiments, the cryopreserved mammalian cells are cryopreserved white blood cells. In some embodiments, the cryopreserved white blood cells are cryopreserved granulocytes, cryopreserved monocytes, cryopreserved lymphocytes, or combinations thereof. In some embodiments, the cryopreserved granulocytes are cryopreserved neutrophils, cryopreserved eosinophils, cryopreserved basophils, or combinations thereof. In some embodiments, the cryopreserved lymphocytes are cryopreserved T cells, cryopreserved B cells, cryopreserved natural killer (NK) cells, or combinations thereof.

In some embodiments, greater than 50% of the thawed cells are viable. In some embodiments, greater than 70% of the thawed cells are viable. In some embodiments, greater than 80% of the thawed cells are viable.

In some embodiments, in step (b) of the methods described above, the amount of the cryopreservation solution by volume is 2 to 4 times greater than the amount of the plurality of hydrogel beads by weight.

In some embodiments, in step (c) of the methods described above, the thawed cells and the plurality of hydrogel beads are incubated at room temperature. In some embodiments, in step (c), the thawed cells and the plurality of hydrogel beads are incubated for 1 to 20 minutes. In some embodiments, in step (c), the thawed cells and the plurality of hydrogel beads are incubated with mixing.

In some embodiments, in step (d) of the methods described above, separating the thawed cells from the plurality of hydrogel beads comprises aspiration, filtration, centrifugation, or a combination thereof.

In some embodiments, methods further include repeating steps (b)-(d) using an additional plurality of hydrogel beads.

As used herein, the term "cryopreserved cells" refers to cells that have been subjected to cryopreservation, e.g., cryopreserved cells stored at −80° C. or below.

As used herein, the term "thawed cells" refers to cells that have been subjected to cryopreservation and then thawed, e.g., thawed lymphocytes for use in laboratory or clinical settings.

As used herein, the phrase "white blood cells" refer to blood cells that are made in the bone marrow and found in the blood and lymph tissue. Non-limiting examples of white blood cells include granulocytes (e.g., neutrophils, eosinophils, basophils), monocytes, and lymphocytes (e.g., T cells, B cells, natural killer (NK) cells).

As used herein, the terms "cryopreserving" or "cryopreservation" refer to the process of cooling cells either by slow-freezing or vitrification. In general, cryopreservation is used to maintain cells in a preserved or dormant state at a temperature below 0° C., after which time the cells are returned to a temperature above 4° C. for subsequent use. In some examples, cryopreservation involves cooling cells to a temperature below about −5° C., −10° C., −20° C., −60° C., −80° C., or about −180° C., for example, in liquid nitrogen or liquid helium, carbon dioxide ("dry-ice"), or slurries of carbon dioxide with other solvents.

As used herein, the term "cryoprotective agent," "cryoprotectant," or "CPA" refers to a compound used to slow, inhibit, or prevent ice nucleation, ice crystal growth, ice formation, or any combination thereof. Cryoprotectants are generally agents with high water solubility and low toxicity. Included within this term are both permeating (e.g., glycerol, ethylene glycol, 1,2-propanediol, and DMSO) and non-permeating (e.g., sugars, dextran, polyvinyl pyrrolidone and hydroxyethyl starch) cryoprotectants. Non-limiting examples of cryoprotectants for use in hydrogel beads described herein are ethylene glycol, glycerol, 1,2-propanediol, DMSO, and sugars (e.g., sucrose, trehalose, raffinose, stachyose, and dextran).

As used herein, the term "cryoprotective solution" refers to a solution (e.g., any physiological solution such as PBS) that includes one or more cryoprotective agents. A cryoprotective solution can be supplemented with one or more components including, but not limited to, ions, serum, proteins, penicillin/streptomycin, lipids, salts, formamide, methoxylated compounds, and polymers (e.g., polyvinyl pyrrolidone and polyvinyl alcohol).

As used herein, the term "hydrogel bead" refers to a substance formed when an organic polymer (biological polymer, synthetic polymer, or a combination thereof) is cross-linked via covalent, ionic, or hydrogen bonds to create a three-dimensional open-lattice spherical structure that entraps water molecules to form a spherical bead.

In some examples, the hydrogel beads described herein can be free of cells. In such instances, cells are not encapsulated in the hydrogel beads described herein. As such, the hydrogel beads described herein form a cryoprotective agent delivery and removal system that can be added to a cell suspension without initially encapsulating the cells within the hydrogel beads.

As used herein, "tunable" as used in connection with "tunable" hydrogel beads refers to the ability to adjust different properties of the hydrogel bead to modulate uptake and release of cryoprotective agent from the hydrogel bead. Non-limiting properties of the hydrogel bead that can be used to modulated uptake and release of cryoprotective agent include bead size, bead volume, bead weight, bead diameter, bead material, and combinations thereof.

For example, the size of the hydrogel bead can be varied to achieve the desired rate of uptake and/or release of cryoprotective agent from the hydrogel bead. As shown in FIG. 11, the rate of release of cryoprotective agent increases as the size of the hydrogel bead increases.

Alternatively, or in addition, the concentration of cryoprotective agent within the hydrogel bead can be varied by equilibrating the hydrogel bead in a solution of cryoprotective agent at twice the concentration desired in the hydrogel bead (e.g., if the desired concentration of cryoprotective agent within the hydrogel bead is 5%, 10%, or 20%, then the hydrogel beads are equilibrated in a solution of cryoprotective agent at 10%, 20%, or 40%, respectively). Accordingly, hydrogel beads can be loaded with cryoprotective agent at a concentration of 2.5-50% (v/v) by simply placing the hydrogel beads in a solution of cryoprotective agent that is twice the desired concentration of cryoprotective agent in the hydrogel bead, where mixture includes 1 g of hydrogel beads/1 mL solution of cryoprotective agent.

As used herein, the term "incubating" refers to maintaining a state of controlled conditions such as temperature over a period of time to achieve the desired results, e.g., to achieve loading of the hydrogel beads with one or more cryoprotective agents.

As used herein, the term "isotonic solution" refers to a solution having substantially the same osmotic pressure as a cell, e.g., white blood cells, such as a lymphocyte, such that there is substantially no net flow of water ions into or out of the cells.

As used herein, "loading" refers to uptake of the cryoprotective agent by the hydrogel bead and/or the lymphocyte. After uptake of the cryoprotective agent, the hydrogel bead and the lymphocyte can be referred to as the loaded hydrogel bead and the loaded lymphocyte, respectively. The amount of cryoprotective agent "loaded" into the hydrogel bead or lymphocyte can be expressed as a ratio, e.g., the volume of cryoprotective agent to the volume of the hydrogel bead.

As used herein, "unloading" refers to release of the cryoprotective agent by the hydrogel bead and/or the lymphocyte. After release of the cryoprotective agent, the hydrogel bead and the lymphocyte can be referred to as the unloaded hydrogel bead and the unloaded lymphocyte, respectively. The amount of cryoprotective agent "unloaded" from the hydrogel bead or lymphocyte can be expressed as a ratio, e.g., the volume of cryoprotective agent to the volume of the hydrogel bead.

As used herein, "lymphocytes" refers to immune cells made in the bone marrow and found in the blood and lymph tissue. Non-limiting examples of lymphocytes include T cells, B cells, and natural killer (NK) cells.

As used herein, "cryopreserved lymphocytes" refers to lymphocytes that have been subjected to cryopreservation, e.g., cryopreserved lymphocytes stored at −80° C.

As used herein, "thawed lymphocytes" refers to lymphocytes that have been subjected to cryopreservation and then thawed, e.g., thawed lymphocytes for use in laboratory or clinical settings.

As used herein, "mixture" refers to a combination of two or more substances in physical contact with one another, e.g., a mixture of lymphocytes suspended in solution and hydrogel beads.

As used herein, "separating" refers to the process of removing a substance from another (e.g., removing hydrogel beads or cells such as lymphocytes from a mixture). The process can employ any technique known to those of skill in the art, e.g., decanting the mixture, aspirating liquids from the mixture, centrifuging the mixture, filtering the hydrogel beads from the mixture, or a combination thereof.

As used herein, the term "(v/v)" refers to the concentration of solute expressed as a volume percentage, e.g., the concentration 1% (v/v) refers to a solution with 1 ml of solute (e.g., the cryoprotective agent) dissolved in a 100 ml of solution, which includes both the solute (e.g., the cryoprotective agent) and the solvent (e.g., the cryoprotective solution).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

Various aspects and embodiments will be described with reference to the following figures. The figures are not necessarily drawn to scale.

Figure 1:
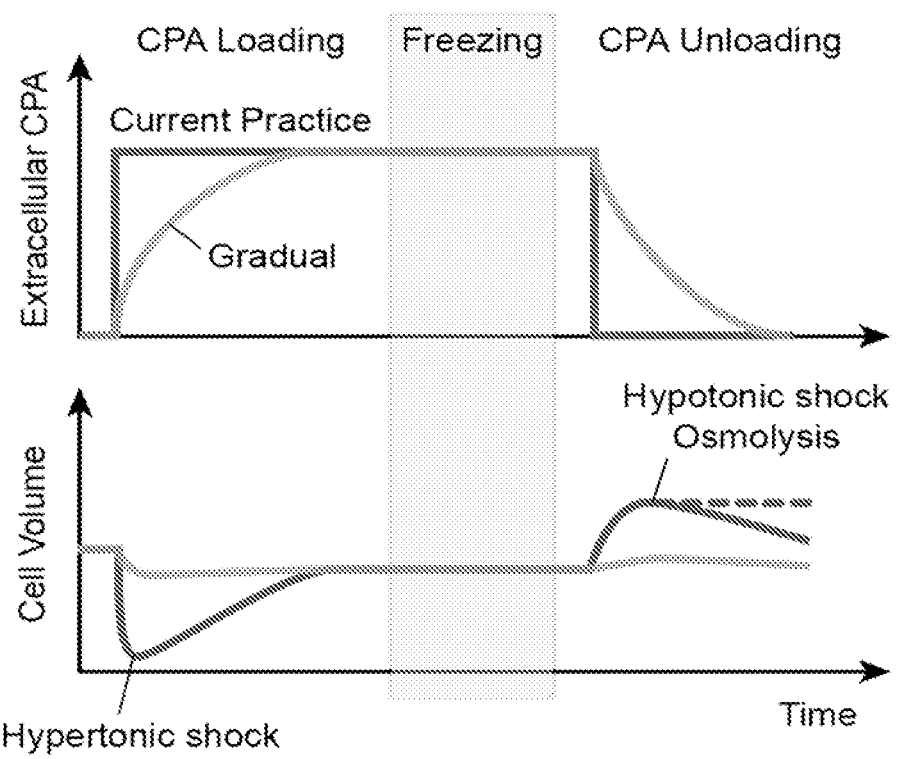
FIG. 1 is a pair of graphs showing changes in extracellular CPA levels (top) and Cell Volume (bottom) from gradual CPA loading and unloading as described herein using hydrogel beads (light gray curved line in the top graph and mostly horizontal light gray line in the bottom graph) avoids osmotic damage from cryopreservation media using current practice methods (vertical and horizontal black line in the top graph and sharply curved black lines showing hypertonic shock and hypotonic shock in the bottom graph that is avoided by methods described herein).

The details of one or more embodiments of the invention are set forth in the description below. Other features or advantages of the present invention will be apparent from the following drawings and detailed description of several embodiments, and also from the appended claims.

DETAILED DESCRIPTION

The present disclosure is based, at least in part, on the development of hydrogel beads that exchange cryoprotective agents with cell media at prescribed rates and methods of use of such hydrogel beads to obtain significantly higher percentages of viable cells, such as white blood cells, e.g., lymphocytes, after cryopreservation compared to cryopreservation methods that use conventional media dilution.

Accordingly, feasibility of a clinically useful method to avoid osmotic damage to human lymphocytes during cryopreservation by distributed and gradual CPA loading and unloading with semipermeable hydrogel beads was established. This addresses a critical barrier to faithful cryopreservation of human immune cells for cell therapy and regenerative medicine applications. The studies described herein pave the way towards preclinical studies of primary lymphocyte and/or engineered T cell preservation.

There is growing clinical interest in processing patient derived immune cells outside of the body to amplify or augment anticancer functions. For example, chimeric antigen receptor (CAR) T cell therapy has been demonstrated to enable long-term survival of patients with refractory leukemias or lymphomas[2]. Likewise, tumor infiltrating lymphocytes (TILs) isolated and activated ex vivo can achieve complete remission of metastatic melanoma[3] and metastatic cervical cancer[1]. Beyond cancer, clinical interest in T cell therapies is growing for treating other ailments such as graft vs host disease[14] and infections in immune compromised individuals[15]. Altogether these groundbreaking recent clinical outcomes indicate that immune cell therapies are quickly becoming, alongside small molecule and biologic drugs, a new third pillar of medicine[16].

Cryopreservation is an essential step in the production and delivery of immune cell therapies. The CAR T therapy production workflow is an illustrative example. Following leukapheresis collection of peripheral mononuclear blood cells (PBMCs) from the patient, PBMCs must undergo viral transfection, selection, expansion, harvest, and quality assurance testing in strict accordance with Good Manufacturing Practices (GMP) in automated closed systems[17]. Commercial manufacturing of CAR T by highly controlled processes requires dedicated centralized facilities which are physically disconnected from the clinic, necessitating cryopreservation for transportation and banking of both PBMC precursors and CAR T cells[8]. These inescapable clinical needs for dedicated GMP facilities are shared by all cell therapies including TIL production[18]. Robust cryopreservation will be a critical enabling technology for dissemination of cell therapies[7,19,20].

Despite this rapidly growing need, clinical practice around immune cell preservation remains inadequate, unreliable, and harmful to patients. PBMC recovery is a critical problem: insufficient T cell yield resulted in a failure to manufacture CART cells for 5 of 38 (13%) patients enrolled in a trial to treat adults with lymphoma[10], and ⅕ (20%) of patients in a trial for neuroblastoma[9]. Median recovery rates of primary PBMCs from healthy donors using optimized cryopreservation practices is only 59%, and the recovery rate of T cells is only 30-40%[11]. Regulatory T (Treg) cells fared even worse in the same study; no memory Tregs survived cryopreservation. Furthermore, cryopreservation induces unreliable phenotypic changes in immune cells. Cryopreservation induces the transition of some primary human CD8+ T cells to a CD4−/CD8low 'double negative' T subset over the course of 24 hours[11]. Cryopreservation significantly alters the cytokine production profile of PBMCs, but these changes can be highly variable between different donor populations[13,21]. Finally, current cell therapy delivery practices cause patients to be unnecessarily exposed to harmful amounts of cryoprotective agents (CPAs), which are chemicals, which must be included in the cryo media at molar concentrations to prevent cell death during freezing. The co-injection of 10-20 mL of dimethyl sulfoxide (DMSO) along with CAR T cells is widely acknowledged to be responsible for the nausea and vomiting experienced by 40-60% of patients[22,23], and is implicated in sometimes life-threatening neurological complications such as encephalopathy (34%), aphasia (18%), tremors (29%), and delirium (29%)[24-27]. Regrettably, this exposure is medically unnecessary and only permitted due to the unacceptably low and unreliable recovery rate of exchanging the cryo media with centrifugal cell washing before transfusion (for hematopoietic stem cells, 60% on average)[28].

Selective perturbation and cell death of lymphocytes can be mitigated by halting osmotic damage during cryo-media exchange. Cryopreservation is a perilous and violent process that exposes cells to extreme biochemical and osmotic stresses. To help prevent intracellular ice formation during freezing, cell penetrating CPAs such as DMSO and glycerol are included in cryopreservation media at very high concentrations (e.g., 10% v/v). As a result, cryopreservation media have a dramatically higher osmolality (>1800 mOsm/kg) than physiological or growth medium (~300 mOsm/kg) and cells experience hypertonic and hypotonic shock when washed into and out of cryo medium (FIGS. 1A and 1B). Cryopreservation outcome is largely mediated by a cell's permeabilities to CPA and water: less permeable cells are more susceptible to osmotic damage and osmolysis. Although data is sparse, one recent study reported the permeability of T cells to be lower than other cell types[29].

No clinically useful method currently exists to mitigate osmotic damage during cryopreservation. Osmotic shock should be avoided by gradual CPA loading and unloading (un/loading), where the extracellular CPA concentration is increased gradually before freezing, and then decreased gradually after thawing (FIG. 1). Manual un/loading by dropwise CPA addition and dilution remains the laboratory recommended method, but it is imprecise, unscalable, and non-uniform: some cells momentarily experience high concentrations of CPA. Even brief exposure to >10% v/v DMSO decreases membrane stability, induces apoptosis, affects stem cell differentiation, and inhibits CD8+ lymphocyte activity, among other effects[30-34]. A clinically useful method must be scalable to large sample volumes: a CAR T transfusion contains on the order of 1 billion cells, and a typical leukapheresis product contains roughly 7-10 billion cells. Furthermore, the system must be extremely simple and reliable: both patient cells and engineered cell products are extraordinarily precious. Finally, an optimal system would also be cost effective, simple to use, and easily deployed in a primary care setting. To date, the only attempts to automate CPA un/loading have been microfluidic devices, but these are complex and with throughputs orders of magnitude too low for translational research and clinical applications (2-10 μL/min)[35-37]. Scaling these devices to large sample volumes is infeasible since cells must stay within the device for the duration of the process (up to several minutes), requiring a large processing volume. Altogether, a clinically useful method of loading and unloading primary lymphocytes with CPAs while simultaneously protecting them from osmotic damage would significantly improve cryopreservation outcome and represent a major advancement in clinical cryopreservation for immunotherapy and regenerative medicine.

Figure 2:
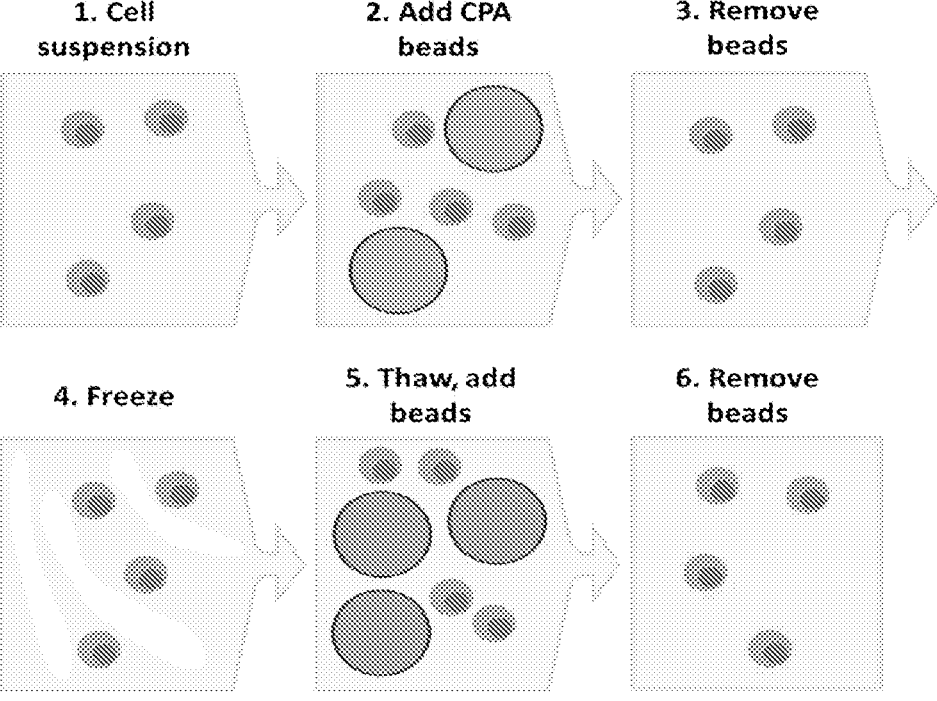
FIG. 2 is a schematic depiction of the overall process described herein showing when the hydrogel beads are added and removed during the process of cryopreservation and thawing of the cells.

To address this expanding clinical need, a distributed system that can perform gradual CPA loading and unloading at a programmable rate uniformly throughout the suspension is developed. This will allow all cells to undergo the identical optimal process at the same time, even for large sample volumes. To achieve this functionality, hydrogel beads with tunable permeability to CPAs are made. Hydrogel beads can slowly release a small molecule payload at a rate controlled by coating permeability. Microscale hydrogel beads in the range 1-5 mm containing a high concentration of CPA are gently mixed with the cell suspension, gradually releasing CPA at a prescribed rate (FIG. 2). Beads are removed immediately before the sample is frozen. This same process is used to gradually remove CPA after thawing: the thawed suspension is immediately mixed with beads bearing fresh media, which leach most of the CPA from the cells at a controlled rate. This technology represents the first use of composite biomaterials and drug delivery principles to load and unload CPAs in large sample volumes, a clinical requirement.

It is becoming increasingly apparent that cell-based immunotherapies, in which the patient's immune cells are isolated and processed ex vivo to boost anticancer functionality, can often achieve complete remission of several otherwise untreatable cancers[1-6]. Cryopreservation of patient immune cells is an essential step in the scaled-up production of these complex new therapies, due to the clinical necessity of using automated closed systems at dedicated facilities[7,8]. Despite the rapidly expanding importance of cryopreservation of immune cells, clinical best practices remain inadequate and unreliable. Cell recovery remains a critical problem: insufficient T cell yield results in manufacturing failure rates of 13%-20% for patients in recent trials[9,10]. Even with laboratory best practices and healthy donors, T cell recovery is only 30%-40%[11,12]. Cryopreservation is also known to selectively induce apoptosis and phenotypic changes in immune cell subtypes of special importance to cell immunotherapy and regenerative medicine such as cytotoxic T cells and regulatory T cells[11,13]. Also, the co-injection of approximately 10 mL of dimethyl sulfoxide (DMSO) along with thawed CAR T cell product is widely acknowledged to be responsible for the nausea and vomiting experienced by up to 60% of patients and is implicated in sometimes life-threatening neurological complications. New methods to alleviate cryo-injury will be required to faithfully preserve human lymphocytes for cell therapy applications.

One of the main mechanisms of cell injury during cryopreservation is osmotic damage to cell membranes caused by cryoprotective agents (CPAs). Very high intracellular concentrations of CPA are required to prevent intracellular ice formation. However, cell membranes are only slightly permeable to CPAs, and current best practices expose cells to extreme osmotic potentials that cause osmotic damage and osmolysys immediately before and after freezing. Dropwise manual dilution, the laboratory best practice, is cumbersome and unscalable for large clinical samples. A clinically feasible method of loading and unloading patient lymphocytes with CPAs while simultaneously protecting them from osmotic damage would significantly improve cryopreservation outcome and represent a major advancement towards reliable preservation of immune cells for immunotherapy.

To address this expanding clinical need, a distributed system that performs gradual CPA loading and unloading throughout the entire suspension at once was developed and is described herein. To achieve this, hydrogel beads for controlled-rate CPA exchange were engineered. Hydrogel beads (1-5 mm) containing CPA were mixed with lymphocytes before cryopreservation to gradually load the lymphocytes with CPA, and then the hydrogel beads were separated from the lymphocytes immediately before freezing. Additionally, hydrogel beads were used to gradually unload CPA after thawing: the thawed suspension was mixed with hydrogel beads bearing fresh media, which gradually leached most of the CPA from the lymphocytes at a controlled rate.

Accordingly, the present disclosure provides, in some aspects, hydrogel beads and methods of using such hydrogel beads during cryopreservation of cells, e.g., white blood cells, such as lymphocytes. Methods of loading hydrogel beads with one or more cryoprotective agent is also within the scope of the present disclosure.

I. Hydrogel Beads Including Cryoprotective Agents

The hydrogel beads described herein can be distributed throughout a suspension of lymphocytes where they act as molecular "sponges" that gradually release and/or absorb cryoprotective agents to and/or from the surrounding solution. As such, cryoprotective agents are loaded and unloaded into and out of cells such as lymphocytes in a gradual and distributed manner that inhibits or prevents osmotic damage to the cells during the cryopreservation process.

The present disclosure provides hydrogel beads having different uptake and release rates (also referred to as exchange rates), which can be finely tuned by adjusting certain properties of the hydrogel beads such as diameter, volume, weight, material, and combinations thereof.

The hydrogel beads can have any diameter suitable for protecting cells from osmotic damage during loading and unloading of cryopreservation agents. For example, the hydrogel bead has a diameter of 1 to 5 mm. In some embodiments, the hydrogel bead has a diameter of 1 to 4 mm, 1 to 3 mm, 1 to 2 mm, 2 to 5 mm, 3 to 5 mm, or 4 to 5 mm.

The hydrogel bead can have any volume suitable for protecting lymphocytes from osmotic damage during loading and unloading of cryopreservation agents. For example, the hydrogel bead has a volume of 0.5 to 65 μL. In some embodiments, the hydrogel bead has a volume of 0.5 to 60 μL, 0.5 to 55 μL, 0.5 to 50 μL, 0.5 to 45 μL, 0.5 to 40 μL, 0.5 to 35 μL, 0.5 to 30 μL, 0.5 to 25 μL, 0.5 to 20 μL, 0.5 to 15 μL, 0.5 to 10 μL, 0.5 to 5 μL, 0.5 to 1 μL, 1 to 65 μL, 5 to 65 μL, 10 to 65 μL, 15 to 65 μL, 20 to 65 μL, 25 to 65 μL, 30 to 65 μL, 35 to 65 μL, 40 to 65 μL, 45 to 65 μL, 50 to 65 μL, 55 to 65 μL, or 60 to 65 μL.

The hydrogel bead can have any weight suitable for protecting lymphocytes from osmotic damage during loading and unloading of cryopreservation agents. For example, the hydrogel bead has a weight of 0.5 to 65 mg. In some embodiments, the hydrogel bead has a weight of 0.5 to 60 mg, 0.5 to 55 mg, 0.5 to 50 mg, 0.5 to 45 mg, 0.5 to 40 mg, 0.5 to 35 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 65 mg, 5 to 65 mg, 10 to 65 mg, 15 to 65 mg, 20 to 65 mg, 25 to 65 mg, 30 to 65 mg, 35 to 65 mg, 40 to 65 mg, 45 to 65 mg, 50 to 65 mg, 55 to 65 mg, or 60 to 65 mg.

The hydrogel bead can be formed from a biological polymer, a synthetic polymer, or a combination thereof. Accordingly, the hydrogel bead comprises a biological polymer, a synthetic polymer, or a combination thereof. Examples of a biological polymer include, but are not limited to, dextran, chitosan, alginate, fibrin, collagen, and gelatin. Examples of a synthetic polymer include, but are not limited to, poly(hydroxyethyl methacrylate) (PHEMA), poly (vinyl alcohol) (PVA), poly(ethylene glycol) (PEG), poly (acrylic acid) (PAA), poly(methacrylic acid) (PMMA), and polyacrylamide (PAA).

The hydrogel bead can comprise any cryoprotective agent or combination of cryoprotective agents suitable for cryopreservation of lymphocytes. For example, the hydrogel bead can comprise DMSO or glycerol or both DMSO and glycerol. Examples of cryoprotective agents include, but are not limited to, sugar, glycerol, ethylene glycol, and dimethyl sulfoxide (DMSO).

The one or more cryoprotective agents can be present in the hydrogel bead at any amount suitable for protecting lymphocytes from osmotic damage during loading and unloading of cryopreservation agents. For example, the one or more cryoprotective agents is present in the hydrogel bead at an amount of 2.5% to 50% (v/v). In some embodiments, the one or more cryoprotective agents is present in the hydrogel bead at an amount of 2.5% to 45% (v/v), 2.5% to 40% (v/v), 2.5% to 35% (v/v), 2.5% to 30% (v/v), 2.5% to 25% (v/v), 2.5% to 20% (v/v), 2.5% to 15% (v/v), 2.5% to 10% (v/v), 2.5% to 5% (v/v), 5% to 50% (v/v), 10% to 50% (v/v), 15% to 50% (v/v), 20% to 50% (v/v), 25% to 50% (v/v), 30% to 50% (v/v), 35% to 50% (v/v), 40% to 50% (v/v), or 45% to 50% (v/v).

Also within the scope of the present disclosure are compositions comprising a plurality of hydrogel beads described herein. For example, the composition can comprise the plurality of hydrogel beads and a solution comprising one or more cryoprotective agents. Compositions provided herein can also comprise an additional components such as a buffer, a preservative, a stabilizer (e.g., a pH stabilizer), a surfactant, an antimicrobial agent, or a combination thereof.

II. Methods of Preparing Hydrogel Beads Including Cryoprotective Agents

Also provided herein are methods for preparing hydrogel beads comprising one or more cryoprotective agents. Such methods can also be referred to as loading the hydrogel beads with one or more cryoprotective agents.

Methods for loading hydrogel beads described herein produce hydrogel beads in which each hydrogel bead comprises one or more cryoprotective agents at an amount of 2.5% to 50% (v/v). In some examples, hydrogel beads in which each hydrogel bead comprises one or more cryoprotective agent at an amount of 2.5% to 45%, 2.5% to 40%, 2.5% to 35%, 2.5% to 30%, 2.5% to 25%, 2.5% to 20%, 2.5% to 15%, 2.5% to 10%, 2.5% to 5%, 5% to 50%, 10% to 50%, 15% to 50%, 20% to 50%, 25% to 50%, 30% to 50%, 35% to 50%, 40% to 50%, or 45% to 50% (v/v).

To load the hydrogel beads with one or more cryoprotective agents, the hydrogel beads are incubated with a cryoprotective solution comprising one or more cryoprotective agents, and then the hydrogel beads are separated from the cryoprotective solution. The hydrogel beads can be separated from the cryoprotective solution using any method known in the art such as aspiration, filtration, centrifugation, or a combination thereof.

The hydrogel beads can be incubated with any amount of one or more cryoprotective agents suitable for uptake of the one or more cryoprotective agents by the hydrogel beads.

For example, the hydrogel beads can be incubated with a cryoprotective solution comprising one or more cryoprotective agents at a concentration of 2.5% to 50% (v/v). In some embodiments, the hydrogel beads can be incubated with a cryoprotective solution comprising one or more cryoprotective agents at a concentration of 2.5% to 45%, 2.5% to 40%, 2.5% to 35%, 2.5% to 30%, 2.5% to 25%, 2.5% to 20%, 2.5% to 15%, 2.5% to 10%, 2.5% to 5%, 5% to 50%, 10% to 50%, 15% to 50%, 20% to 50%, 25% to 50%, 30% to 50%, 35% to 50%, 40% to 50%, or 45% to 50% (v/v).

In another example, the hydrogel beads and the cryoprotective solution comprising one or more cryoprotective agents at a concentration of 2.5% to 50% (v/v) can be incubated such that the volume of the cryoprotective solution is 5 to 20 times greater than the total volume of the hydrogel beads. In some embodiments, the volume of the cryoprotective solution is 10 to 20 times, 15 to 20 times, 5 to 15 times, or 5 to 10 times greater than the total volume of the hydrogel beads.

The hydrogel beads can be incubated with one or more cryoprotective agents for a suitable time and temperature to allow uptake of the one or more cryoprotective agents by the hydrogel beads. For example, the hydrogel beads and one or more cryoprotective agents can be incubated for 1 to 60 minutes at 4° C. to 37° C. (e.g., at 25° C., room temperature). In some embodiments, the hydrogel beads and one or more cryoprotective agents are incubated are incubated for 1 to 50 minutes, 1 to 40 minutes, 1 to 30 minutes, 1 to 20 minutes, 1 to 10 minutes, 1 to 5 minutes, 5 to 60 minutes, 10 to 60 minutes, 20 to 60 minutes, 30 to 60 minutes, 40 to 60 minutes, or 50 to 60 minutes.

The hydrogel beads and the cryoprotective solution comprising one or more cryoprotective agents can be incubated with mixing, for example, by manual or mechanical shaking or rocking.

Any hydrogel beads including those known in the art or described herein can be loaded with one or more cryoprotective agents according to methods described herein. In some examples, methods described herein can be used to load hydrogel beads obtained from commercial sources or synthesized by any method known in the art (e.g., by microfluidic droplet generation). Accordingly, methods described herein can comprise synthesizing the hydrogel beads, loading the synthesized hydrogel beads with one or more cryoprotective agents, and then separating the synthesized hydrogel beads loaded with one or more cryoprotective agents.

After separating the hydrogel beads from the cryoprotective solution, the hydrogel beads comprising one or more cryoprotective agents can be stored in a sterile airtight container for future use. In some examples, the hydrogel beads can be stored under cold conditions, e.g., at 4° C., for several weeks or months, e.g., for up to 2 months or more before use.

III. Uses of Hydrogel Beads Comprising Cryoprotective Agents

The hydrogel beads described herein can be used to load and unload cryoprotective agents into and out of cells in a gradual and distributed manner that inhibits or prevents osmotic damage to the lymphocytes during the cryopreservation process. This is achieved by using hydrogel beads that have controlled release of the cryoprotective agents that is fine tunable to accommodate various volumes and amounts of cells, and by distributing the hydrogel beads throughout the suspension of cells.

For example, when loading lymphocytes with cryoprotective agents prior to cryopreservation, the lymphocytes can be incubated with hydrogel beads comprising cryoprotective agents, which are gradually released from the hydrogel beads dispersed throughout the suspension of lymphocytes, thereby enabling gradual and distributed uptake of the cryoprotective agents by the lymphocytes.

In another example, when unloading cryoprotective agents from lymphocytes after cryopreservation, hydrogel beads free or substantially free of cryoprotective agents can be dispersed throughout the suspension of lymphocytes, thereby enabling gradual and distributed uptake of the cryoprotective agents by the hydrogel beads.

Any lymphocytes can be cryopreserved and recovered using methods described herein. Non-limiting examples of lymphocytes include, but are not limited to, T cells, B cells, or natural killer (NK) cells.

Any cells suitable for cryopreservation can be used in methods described herein including, but not limited to, animal cells (e.g., mammalian cells such as human cells), plant cells, bacterial cells, and fungal cells. A heterogeneous suspension of cells or a homogenous suspension of cells can be cryopreserved according to methods described herein.

Any amount of cells can be cryopreserved and recovered using methods described herein. For example, methods described herein can involve volumes and amounts of cells used for research purposes, e.g., 10 μL to 10 mL volumes and 100 to 100,000 cells. In another example, methods described herein can involve volumes and amounts of cells used for clinical purposes, e.g., 50 to 500 mL volumes and $1.0\times10^6$ to $1.0\times10^{10}$ cells such as lymphocytes.

The hydrogel beads and the cells can be incubated without mixing or with mixing, for example, by manual or mechanical shaking or rocking.

The hydrogel beads used in methods described herein can be obtained by synthesis or from commercially available sources. Accordingly, methods described herein can comprise synthesizing the hydrogel beads and then using the synthesized hydrogel beads for cryopreservation of cells and/or for recovering cryopreserved cells.

A. Cryopreservation of Cells

In some embodiments, methods described herein are used to cryopreserve cells using any of the hydrogel beads described herein. In such instances, the cells are suspended in an isotonic solution, hydrogel beads loaded with cryoprotective agents are added to the isotonic solution, and then the isotonic solution is incubated for a time and under conditions sufficient to release the cryoprotective agents from the hydrogel beads and into the isotonic solution where the cryoprotective agents can be absorbed by the cells. Following loading of the cells with cryoprotective agents, the cells can be separated from the hydrogel beads and cooled to a temperature sufficient to cryopreserve the cells (e.g., −80° C.).

Any isotonic solution can be used to suspend cells for cryopreservation according to methods described herein. Non-limiting examples of isotonic solutions include phosphate buffered saline (PBS) and cell culture media. The volume of isotonic solution used in methods described herein can be 1 to 10 times greater than the total weight of the hydrogel beads. In some examples, the volume of isotonic solution is 1 to 9 times, 1 to 8 times, 1 to 7 times, 1 to 6 times, 1 to 5 times, 1 to 4 times, 1 to 3 times, 1 to 2 times, 2 to 10 times, 3 to 10 times, 4 to 10 times, 5 to 10 times, 6 to 10 times, 7 to 10 times, 8 to 10 times, or 9 to 10 times greater than the total weight of the hydrogel beads.

After the hydrogel beads are added to the isotonic solution, the resulting mixture of hydrogel beads and cells is incubated for a suitable time and temperature to allow release of the cryoprotective agents by the hydrogel beads and uptake by the cells. For example, the hydrogel beads loaded with one or more cryoprotective agents and the cells can be incubated for 1 to 60 minutes at 4° C. to 37° C. (e.g., at 25° C., room temperature). In some embodiments, the hydrogel beads loaded with one or more cryoprotective agents and the cells are incubated for 1 to 50 minutes, 1 to 40 minutes, 1 to 30 minutes, 1 to 20 minutes, 1 to 10 minutes, 1 to 5 minutes, 5 to 60 minutes, 10 to 60 minutes, 20 to 60 minutes, 30 to 60 minutes, 40 to 60 minutes, or 50 to 60 minutes.

After loading the cells with cryoprotective agents and prior to cryopreservation, the hydrogel beads can be separated from the isotonic solution using any method known in the art such as aspiration, filtration, centrifugation, or a combination thereof. The cells loaded with cryoprotective agents can then be cooled to a temperature sufficient to cryopreserve the cells (e.g., –80° C.) and stored for future use (e.g., research or clinical purposes).

B. Thawing of Cryopreserved Cells

In some embodiments, methods described herein are used to thaw and recover cells that have been cryopreserved. In such instances, the cryopreserved cells are thawed at a temperature above freezing, hydrogel beads free or substantially free of cryoprotective agents are added to the thawed cells, and then the hydrogel beads and the thawed cells are incubated for a time and under conditions sufficient for the cryoprotective agents to be released from the thawed cells into the surrounding solution and then absorbed by the hydrogel beads.

The thawed cells can then be separated from the hydrogel beads and used in various application including research and clinical purposes. For example, when the thawed cells are immune cells, the thawed cells can be used for immunotherapy. The hydrogel beads can be separated from the thawed cells using any method including those known in the art or described herein.

In some instances, additional hydrogel beads free or substantially free of cryoprotective agents can be added the to the separated cells to absorb any remaining cryoprotective agents. Accordingly, methods for recovering cryopreserved cells can comprise one or more rounds of adding hydrogel beads to the thawed cells, incubating the hydrogel beads and the thawed cells, and separating the cells from the hydrogel beads.

Methods described herein protect cells from osmotic damage during unloading of cryoprotective agents following cryopreservation, and therefore enable recovery of high yields of viable thawed cells. For example, following methods described herein, greater than 50%, greater than 60%, greater than 70%, greater than 80%, or greater than 90% of the thawed cells are viable.

The amount of beads used in methods described herein for recovering cryopreserved cells depends on the volume of the solution in which the thawed cells are suspended. For example, the volume of cryopreservation solution in which the cells are thawed is 1 to 10 times greater than the total weight of the hydrogel beads. In some examples, the volume of cryopreservation solution is 1 to 9 times, 1 to 8 times, 1 to 7 times, 1 to 6 times, 1 to 5 times, 1 to 4 times, 1 to 3 times, 1 to 2 times, 2 to 10 times, 3 to 10 times, 4 to 10 times, 5 to 10 times, 6 to 10 times, 7 to 10 times, 8 to 10 times, or 9 to 10 times greater than the total weight of the hydrogel beads.

After the hydrogel beads are mixed with the thawed cells, the resulting mixture of hydrogel beads and thawed cells is incubated for a suitable time and temperature to allow release of the cryoprotective agents by the thawed cells and uptake by the hydrogel beads. For example, the hydrogel beads and the thawed cells can be incubated for 1 to 60 minutes at 4° C. to 37° C. (e.g., at 25° C., room temperature). In some embodiments, the hydrogel beads and the thawed cells are incubated are incubated for 1 to 50 minutes, 1 to 40 minutes, 1 to 30 minutes, 1 to 20 minutes, 1 to 10 minutes, 1 to 5 minutes, 5 to 60 minutes, 10 to 60 minutes, 20 to 60 minutes, 30 to 60 minutes, 40 to 60 minutes, or 50 to 60 minutes.

After unloading the cryoprotective agents from the thawed cells and prior to using the thawed cells in a research or clinical application, the hydrogel beads can be separated from the thawed cells using any method known in the art such as aspiration, filtration, centrifugation, or a combination thereof.

EXAMPLES

In order that the invention described may be more fully understood, the following examples are set forth. The examples described in this application are offered to illustrate the methods and compositions provided herein and are not to be construed in any way as limiting their scope.

Example 1: Development and Characterization of Hydrogel Beads with Controlled Rates of Continuous CPA Uptake and Release The objective is to synthesize and characterize semipermeable hydrogel beads that will either add or remove CPAs from cell media at prescribed rates. The main deliverable is a method to routinely synthesize semipermeable microscale gel beads for any desired rate of CPA uptake or release at a given temperature within the nominal range of 0.2-15 minutes. A secondary deliverable is a dynamical model of cell osmotic potential and CPA concentration over time to allow rational design.

1.1: Synthesize Semipermeable Hydrogel Beads for Gradual CPA Uptake and Release

Figure 3:
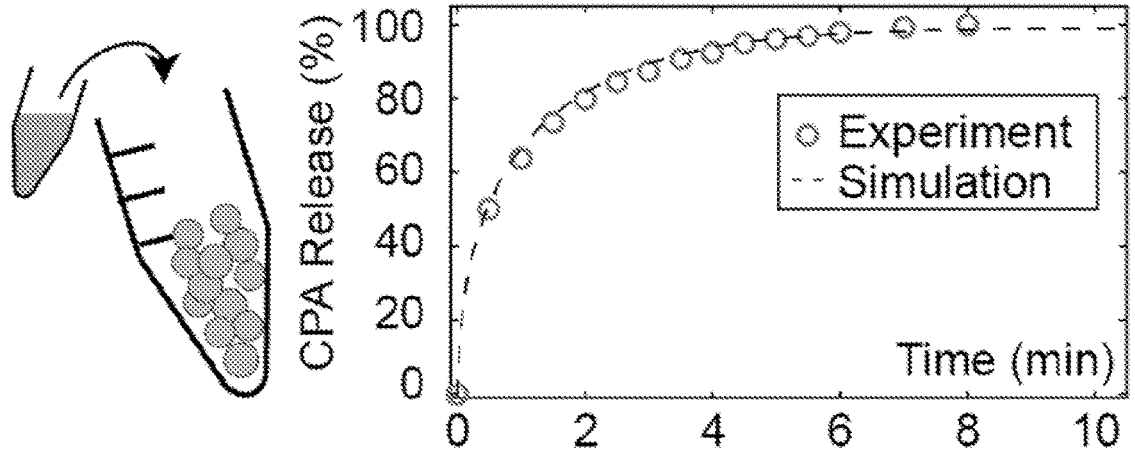
FIG. 3 is a schematic depiction and graph showing gradual release of CPA (e.g., DMSO) from hydrogel beads.

Here, beads 1-5 mm in diameter were synthesized using microfluidic droplet generation and 2% polyacrylamide/bis-acrylamide, following standard oil emulsion methods[43], and beads were synthesized using calcium alginate. Uniform calcium-alginate hydrogel beads were synthesized by dripping 5% alginate from a needle with a surrounding nitrogen gas sheath into a $CaCl_2$ bath. Bead size and uniformity was confirmed by imaging. 5.0 µL beads were incubated for four hours in a 15% DMSO solution, then strained, blotted, and weighed. Beads were then suspended in saline for several minutes under gentle mixing, and the rate of DMSO release was measured over time by sampling the solution and measuring osmolality by micro-osmometer. The rate of release was compared with numerical simulations of diffusion based on the average bead size (FIG. 3). The diffusion coefficient of DMSO within the gel was measured to be $1.0 \times 10^{-5}$ cm$^2$s$^{-1}$ at room temperature, matching expected values[41,42].

1.2: Characterize Semipermeable Hydrogel Beads and Model CPA Transport Dynamics Here, the objective is to develop dynamic models of cell osmotic potential and intracellular CPA concentration over time during gradual loading and unloading, which cannot be measured directly. This allows rational design of CPA uptake and release profiles which minimizes both osmotic damage and extended exposure to high concentrations of intracellular CPA. Experimental results are compared with numerical simulations in COMSOL and analytical models of mass transport and volume changes of both cells and beads. These models are used to design, for example, heterogeneous mixtures of beads with different permeabilities and CPA loads to achieve more complex and less toxic CPA loading and unloading profiles. The deliverable is a simulation framework to predict the effects of different hydrogel bead CPA uptake and release rates on cell CPA loading and unloading.

Expected outcomes and alternative approaches: The key metric of success is the ability to reliably add and then remove CPA from a given sample solution at tunable rates which are predicted by modeling. Bead geometry alone is sufficient to achieve gradual CPA uptake and release. The sample recovery was about 96% without any dilution in these experiments.

Example 2: Analysis of CPA Loading and Unloading with Hydrogel Beads for T Cell Cryopreservation In this example, the rates of DMSO loading and unloading that maximizes T cell viability will be determined. The rate of CPA loading will be different than the rate of unloading, because CPA loading and unloading is conventionally performed at 4° C. to 37° C., and cell membrane CPA permeability depends on temperature. In both cases, it is likely that T cell viability is highest at some intermediate rate in the range of 0.2-10 minutes, decreasing for instant un/loading due to osmotic shock/osmolysis and for extended un/loading (e.g., >10 minutes) due to CPA cytotoxicity (see Section 2.1 below). Un/loading rates will likely fall close to the DMSO equilibration timescale, which is measured in Section 2.2. To establish proof of principle and ensure good experimental practice, experiments will be performed on Jurkat cells, and then on primary human CD3+ T lymphocytes from healthy donors.

2.1 Relationship Between CPA Loading and Unloading Rates and T Cell Viability Viability of Jurkat cells (see Example 4) and primary human T cells following cryopreservation will be measured with different rates of CPA un/loading using the hydrogel bead system developed in Example 1. For cell line work, the Jurkat clone E6-1 will be thawed and expanded following standard protocols in T-75 flasks at 37° C. and 5% CO$_2$, maintaining cell density between $1.0 \times 10^{-5}$ cell/mL and $3.0 \times 10^{-6}$ cells/mL in T cell growth medium (RPMI-1640+ 10% fetal bovine serum, FBS). Cryopreservation experiments will take place with cells in log phase growth. For primary cell preparation, PBMCs will be isolated from the buffy coat fraction of fresh blood from healthy donors (Research Blood Components, LLC) by centrifugation on Ficoll-Pacque, and CD3+ T lymphocytes will be isolated by sequential B cell depletion (CD19) and T cell enrichment (CD3) by magnetic separation. Cell concentration and viability will be measured by either Sytox Green nuclear stain or MTT exclusion with an imaging cell counter (Nexcelom), then frozen either with the laboratory standard method or gradual CPA un/loading with hydrogel beads. In the standard method, −1 million cells will be resuspended in cryo-medium (50% RPMI/40% FBS/10% DMSO) at 4° C. Cells will be immediately transferred to a refrigerated cryo vial and cooled at 1° C./min to −80° C. in a controlled rate freezer (Planer Kryo). For experiments spanning more than 5 days, cells will be transferred from −80° C. freezer to vapor phase liquid nitrogen. Cells will be thawed rapidly in 37° C. water bath, then diluted and washed in growth medium. Cell recovery and viability will be measured immediately, 1 hour, and 24 hours post-thaw. For gradual un/loading with the beads, the procedure will be identical except isolated T cells will be resuspended in DMSO-free cryo-media (56% RPMI+44% FBS) at 4° C. and a metered dose of 4° C. gel beads containing 10% equivalent DMSO will be added and allowed to equilibrate under gentle mixing. Beads will be removed and the suspension will be frozen as described earlier. For CPA unloading, the thawed sample will be equilibrated with beads containing RPMI at 37° C., followed by dilution and washing in growth medium.

First, it will be verified that the gel beads alone do not affect cell viability and recovery by mixing cells with isotonic beads for up to 15 minutes at 4° C. and 37° C. Cell recovery and viability will be compared with the untreated arm. To test the relative importance of gradual CPA loading vs unloading, three sets of experiments will be performed. The experiment is to test CPA unloading at different rates with hydrogel beads vs instant dilution. Cell aliquots will be frozen identically using the standard procedure, then thawed one by one using each protocol to ensure good practice and avoid unnecessary prolonged exposure to CPA in the faster unloading conditions. The next set of experiments will be reversed: CPA loading at different rates, and then identical thawing by the standard method. The third and final experiment is to combine the rates of loading and unloading found earlier. As mentioned herein, CPA loading and unloading occurs at 4° C. to 37° C. and cell permeability increases with temperature. Furthermore, CPA toxicity is higher at physiological temperatures, benefitting faster unloading. Therefore, loading rates are expected to be slower than unloading rates.

2.2: Measure Permeability of T Cells to CPA and Water

Figure 4:
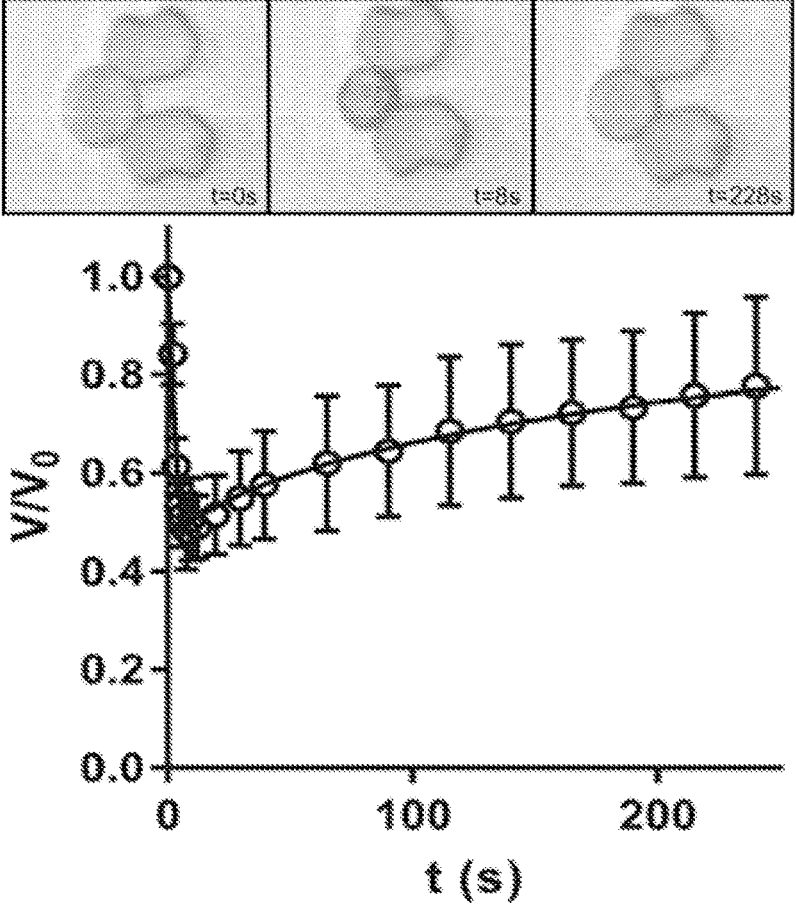
FIG. 4 are images and a graph showing single cell microfluidic measurements of CPA permeability by shrink-swell analysis.

Direct measurements of the permeability of single cells to CPAs and water will be performed using an microfluidic system developed previously by others[46] (FIG. 4). The existing device traps up to 10 cells in the field of view and was modified to allow multiple sequential measurements in a semi-automated fashion. As described in Section 2.1, these experiments will be first conducted with Jurkat cells for establishing proof of principle and good practice before studying primary cells. Cell concentration and viability will be measured beforehand. Permeability measurements will be performed at 4° C., 22° C. and 37° C. using a temperature-controlled microscope stage (Linkam FDCS196). Briefly, a grid of microfluidic cell traps will be populated by flowing cells at $1.0 \times 10^{-5}$ cells/mL while observing under 20x magnification. Once 10 cells are captured, the inlet flow is switched to cryo-media, and the shrink-swell response of the cells to the hypertonic solution is video recorded for 1-3 minutes. The deliverable is the distribution of membrane CPA and water permeabilities of the cells studied in Section 2.1.

Expected Outcomes and Alternative Approaches:

The studies described herein will have determined whether continuous gradual CPA loading and/or unloading improves primary T cell viability following cryopreservation, and the rates that maximize viability will also have been determined. Furthermore, by comparing viability at different un/loading rates with measurements of CPA permeabilities, the relative importance of hypertonic osmotic shock (during loading), hypotonic osmotic shock/osmolysis (during unloading), and CPA cytotoxicity on T cell viability will be elucidated. Additional experiments of cell viability before and after CPA exposure without freezing, to investigate the relative impacts of CPA-associated damage vs. ice formation, will be performed.

Example 3: Validation of Beads for CPA Un/Loading with In Vitro Assays of T Cell Activity, Function, and Phenotype Whether optimized CPA loading and unloading rescues (Section 3.1) T cell functions and/or (Section 3.2) subtype composition following cryopreservation will be tested, compared to best practice methods which are known to result in selective perturbation and death of T cells. For both sets of tests, the three experimental arms were (1) before cryopreservation vs (2) following best practice cryopreservation and (3) following cryopreservation using optimized CPA un/loading from hydrogel beads.

3.1: Functional & Activity Assays of Jurkat (CD4) and Primary T Lymphocyte Activity To measure Jurkat cell and primary CD4+ T cell activity and function, proliferation and IL-2 production following stimulation by anti-CD3 functionalized microwell plate culture will be measured. Surface functionalized anti-CD3 drives activation by receptor cross-linking, and therefore is more specific than mitogen-based methods. Stimulation will be performed following indicated protocols for brief 24-hour stimulation (BD Biosciences). Proliferation will be measured by ATP production via luminescence assay and cell division rate over 24 hours, and IL-2 production will be measured by sandwich ELISA.

Figure 5:
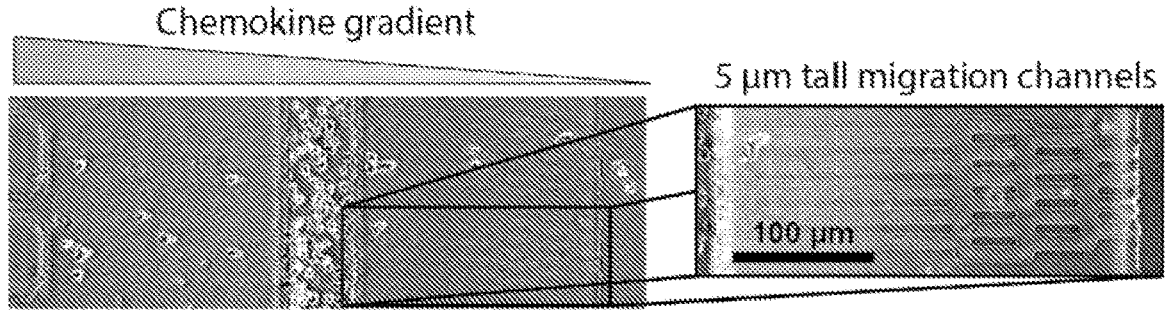
FIG. 5 is a microscope image and an higher magnification inset showing a microfluidic device with numerous migration channels used for an assay of spontaneous and directed migration of CD8+ T lymphocytes.

To test functional activity of CD8+ cytotoxic T cells, directed and spontaneous migration in response to stimulation with SDF1 and IP10 will be quantified. Fibronectin-coated PDMS microfluidic devices will be used (FIG. 5). Chemokine at 1-100 ng/mL will be loaded into the device, then cells will be seeded at 50 million cells/mL and imaged over the course of 4-8 hours. Cell migration towards and away from the chemokine will be tracked in the videos with ImageJ and quantified based on migration directionality (persistence), speed, and migratory cell fraction.

3.2: Composition of Immune Cell Subtypes in CD3+T Fraction

Immune-fluorescence flow cytometry will be performed to test whether gradual CPA un/loading prevents the cryopreservation-induced phenotypic changes in T cell subtype[11]. Similar to viability testing described herein, phenotyping will be repeated immediately, 1 hour, and 24 hours post thaw. These three time points respectively represent cell killing by cryo-injury or osmotic damage, cell responses to perturbation and apoptosis, and cryopreservation-induced changes in proliferation between subtypes. T cell subtype composition will be measured by labeling fresh and cryopreserved primary T cells for CD3, CD4, CD8, and CD19 using direct immunostaining and record with a 6-channel imaging flow cytometer (Amnis Imagestream) following indicated protocols. A fluorescence viability marker such as Sytox will be included in the panel to measure subtype viability at each timepoint.

Expected Outcomes and Alternative Approaches:

The studies described herein will determine whether the known deleterious effects of cryopreservation on T cell function and lymphocyte composition described earlier are rescued with gradual CPA un/loading using semipermeable hydrogel beads. Additionally, T cell function following optimized cryopreservation of isolated primary CD3+ T cells will be compared to recovery from cryopreserved PBMCs, which is the clinical standard practice.

All conditions are tested in triplicate using different donors to control for process errors and donor-to-donor variations. Chiefly, one-way analysis of variance (ANOVA) is employed for each set of experiments, and p-values were calculated using either Dunnett's comparison or Fisher least significance difference based on experiment design.

In summary, this example demonstrates the benefits of a distributed method of gradually loading and unloading CPAs from primary immune cells using semipermeable hydrogel beads as described herein. The present methods address a critical barrier to faithful cryopreservation of human lymphocytes for cell therapy and regenerative medicine applications and paves the way towards preclinical studies of primary lymphocyte and/or engineered T cell preservation. The semipermeable bead system described herein is highly scalable, robust, and easy to use, and it can be a tool for broad use by the larger clinical and research communities.

Example 4: Gradual and Distributed Exchange of Cryoprotective Agents with Hydrogel Beads Protects Jurkat Cells from Osmotic Damage This Example investigated the use of hydrogels as molecular "sponges" to gradually release and/or absorb CPAs from the cell suspension in a distributed manner. In this approach, relatively large (millimeter-scale) hydrogel beads are impregnated with concentrated CPA, then gently mixed with the cell suspension. CPAs diffuse freely within the gel, and the characteristic rate of CPA release increases for larger gels due to the increasing diffusion length scale. For spherical hydrogel beads, this characteristic rate is proportional to the square of bead diameter (Example 5). Controlling the bead size, therefore, allows a degree of control over the maximum rate of CPA uptake and/or release. The concentration of CPA within the beads can be controlled by equilibrating the beads in CPA at 2 times the desired concentration (e.g., if the desired concentration within the beads is 10% CPA, then the beads can be tuned by equilibration in a solution of 20% CPA), while the rate of uptake and release can be tuned based on bead diameter. Accordingly, any size hydrogel bead (e.g., any hydrogel bead having a diameter of 1-5 mm) can be loaded with CPA at a concentration of 2.5-50% (v/v) by simply placing the bead in a CPA solution that is twice the desired concentration, where the loading reaction includes 1 g beads/1 mL CPA solution.

Loading reactions were performed by mixing the synthesized beads in a solution of cryoprotective agents at room temperature. Example loading reactions that result in different amounts of cryoprotective agents are shown in the below table:

| Reaction Number | Size of bead | Amount of Beads Mixed with CPA Solution | % CPA in Cryoprotective Solution | Volume of Cryoprotective Solution Mixed with Beads | Incubation Time | Resulting Concentration of CPA in each Bead |
|---|---|---|---|---|---|---|
| 1 | 3.6 mm | 1 g beads | 30% | 1 mL | 10 min | 15% (v/v) |
| 2 | 2.5 mm | 1 g beads | 15% | 1 mL | 10 min | 7.5% |
| 3 | 4 mm | 1 g beads | 50% | 1 mL | 10 min | 25% |

Figure 6A:
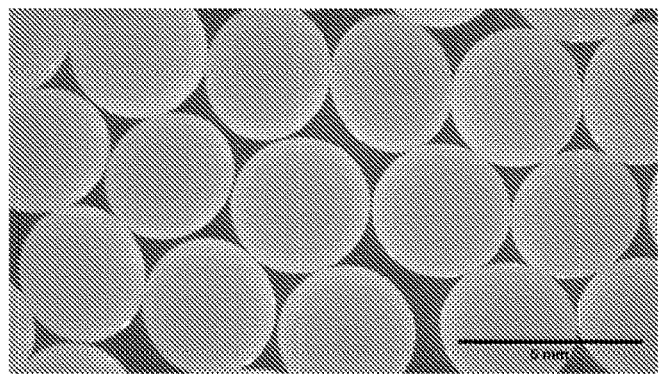
FIG. 6A is an image of calcium alginate hydrogel beads for controlled CPA uptake and release.
Figure 6B:
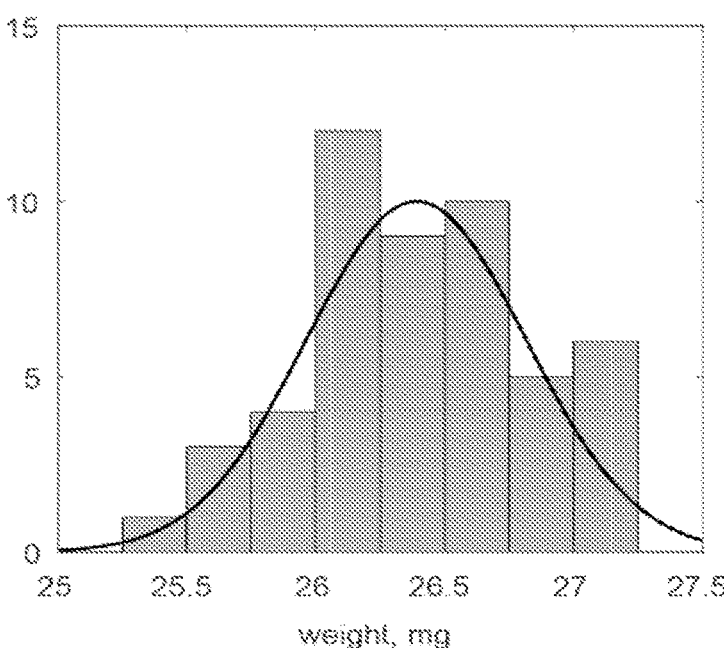
FIG. 6B is a bar graph showing the distribution of bead weight (N=50) with a fitted Gaussian curve.

To test whether hydrogel beads could gradually exchange common cell-penetrating CPAs with the surrounding solution, calcium alginate beads of uniform and controlled size were synthesized using a nitrogen sheath flow apparatus. 5% w/v alginic acid was dissolved in distilled water and dripped at a flow rate of 1 mL/min from a 15G needle into a bath of 200 mM $CaCl_2$. Beads were equilibrated and stored refrigerated in a solution of 50 mM $CaCl_2$ for up to 1 month. The beads were measured to be about 3.6 mm in diameter, with an average mass of about 26.4 mg and a coefficient of variation of about 2% (FIGS. 6A-6B).

Figure 7A:
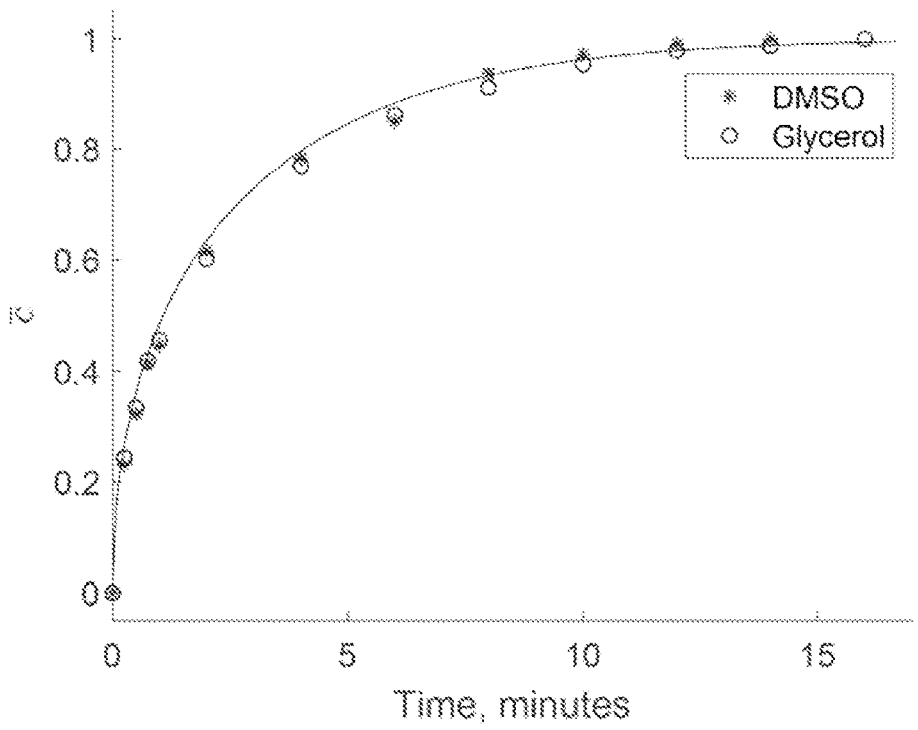
FIGS. 7A-7B are a pair of graphs showing rate of cryoprotective agent uptake (FIG. 7A) and release (FIG. 7B) from calcium alginate beads. The solid line is the solution to numerical model.
Figure 7B:
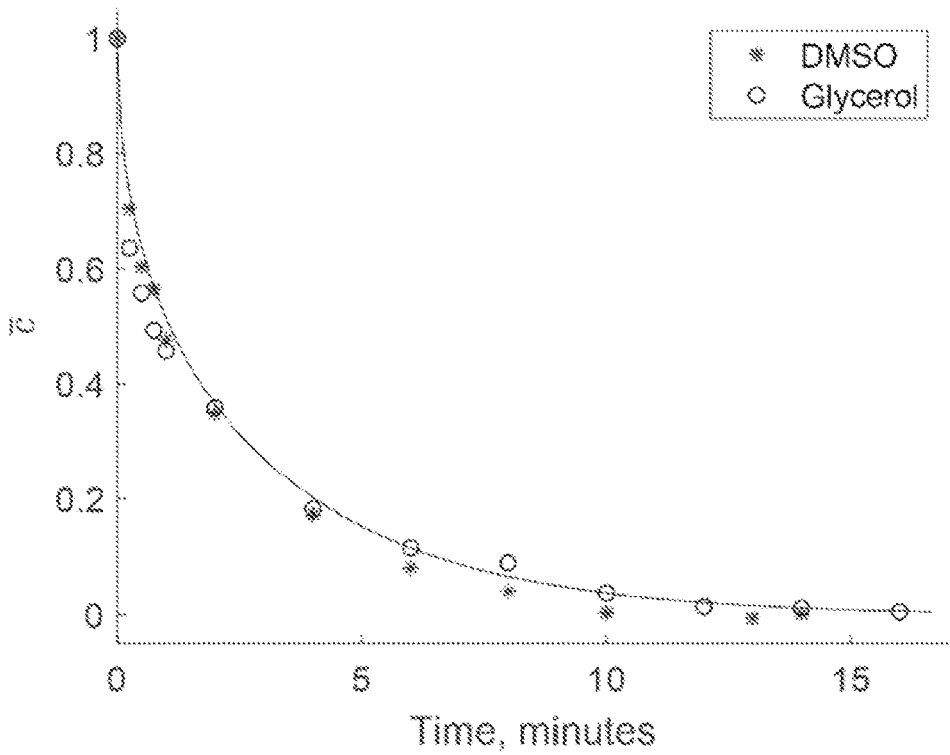

The rate of uptake and release of DMSO and glycerol from the beads was measured by osmometry. To measure CPA release kinetics, about 3 g of beads were equilibrated with a 10% volume ratio solution of glycerol or DMSO in aqueous 50 mM $CaCl_2$ for at least 1 hour. Beads were then removed, blotted in a mesh screen to remove excess liquid, and combined with a 5 mL bath of aqueous 50 mM $CaCl_2$ solution. The mixture was rocked gently for up to 16 minutes, and 50 μL samples of were removed at regular time intervals and measured by osmolarity. The rates of diffusion of DMSO and glycerol into the hydrogel beads was likewise determined by mixing CPA-free beads with a solution of 10% CPA and measuring osmolarity of the solution over time. The normalized change in concentration over time $$\bar{c}(t) = \frac{c(t) - c_0}{c_\infty - c_0}$$

for both uptake and release of glycerol and DMSO is shown in FIG. 7, alongside the results of a numerical result for diffusion from a spherical bead, with for a Coefficient of Diffusion within the hydrogel of $1.5 \times 10^{-5}$ $cm^2$/s and a bead volume 25 μL (Example 5). Altogether, the system reaches 50% of the equilibrium value after about 60 seconds, and 90% after about 6.5 minutes.

Figure 8:
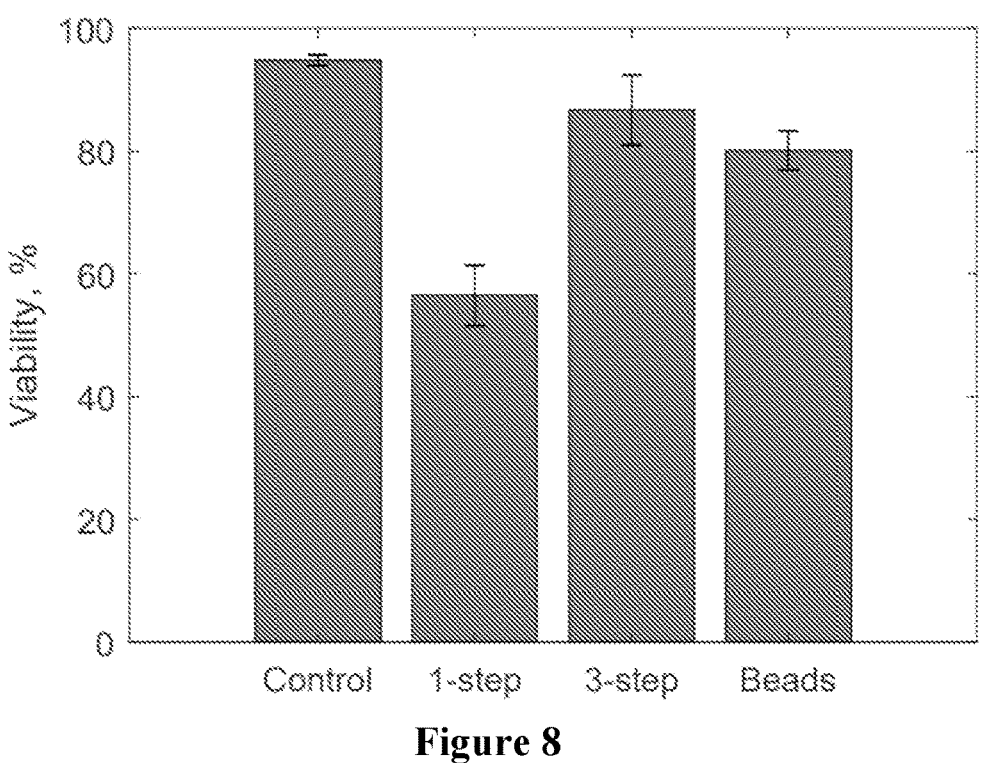
FIG. 8 is a graph showing viability of Jurkat cells loaded with 15% glycerol (N=5) and then unloaded by conventional dilution (1-step or 3-step) or with media exchange using hydrogel beads.

To test whether gradual exchange of CPA using hydrogel beads could prevent or significantly reduce osmotic damage, a room temperature model of CPA-induced hypotonic shock in Jurkat cells was developed. Jurkat cells were equilibrated with a mock cryopreservation solution of 15% (v/v) glycerol in tris-buffered saline with 10 mM $CaCl_2$ ('TBS-C') for 30 minutes, at a concentration of about $0.5 \times 10^6$ cells/mL. The additional calcium ion was included to prevent any changes to calcium alginate gel crosslinking. Cells were then diluted after 10 minutes in glycerol-free TBS-C either by single-step 10× dilution or in three sequential dilutions of 2.17× in five minute intervals. Cells were then washed by centrifugation into complete cell culture medium (RPMI 1640 with 10% fetal bovine serum) and incubated at 37° C. under 5% $CO_2$. After 4 hours, cell number and viability were determined by automatic imaging of propidium iodide exclusion. Single-step dilution resulted in significantly reduced viability compared to either the untreated control or the 3-step dilution (FIG. 8).

To test whether glycerol removal by hydrogel beads would prevent cells from osmotic shock, hydrogel beads were equilibrated with glycerol-free TBS-C buffer for 1 hour, and then blotted to remove excess volume and weighed. An equal mass of beads were mixed gently with the cell suspension (e.g., 2 mL of cells in glycerol+2 g of glycerol-free beads). After five minutes, the cell suspension was aspirated and transferred to a second equal mass of beads prepared identically, and gently mixed for an additional 5 minutes, resulting in a total dilution factor of 4×. Hydrogel bead-mediated glycerol unloading resulted in higher viability compared to the single-step unloading case.

Example 5: Diffusion in a Spherical Bead

5.1. Diffusion from an Isolated Bead with Strong Mixing

A model of the rate of exchange between hydrogel beads impregnated with solute and the surrounding solution was developed. The model was developed starting with a simplified model in which a single particle with radius R and initial solute concentration co is immersed in an infinite volume and subjected to vigorous mixing. In this case the distribution of solute within the sphere as well as the rate of release can be solved analytically. This model provides an upper bound on the maximum rate of release expected in more complex models.

Within the gel, diffusion is governed by Fick's $2^{nd}$ law of diffusion and is described the heat equation. The system is rotationally symmetric. In spherical coordinates, only the radial part of the Laplacian remains:

$$\frac{\partial c}{\partial t} = D \frac{1}{r^2} \frac{\partial}{\partial r}\left(r^2 \frac{\partial c}{\partial r}\right)$$

where D is the diffusion coefficient and c=c(r, t) is concentration with respect to the radial coordinate and time. Initial and boundary conditions are as follows:

Symmetry at origin: $c_r(r=0,t)=0$

Well-mixed open boundary: $c(r=R,t)=0$

Uniform initial values: $c(r,t=0)=c_0$

The general solution is found using separation of variables. Let c(r, t)=P(r)Q(t):

$$\frac{1}{D}PQ' = \frac{1}{r^2}\frac{d}{dr}(r^2 P')Q$$

$$\frac{1}{D}\frac{Q'}{Q} = \frac{P'' + \frac{2}{r}P'}{P} = -\lambda^2$$

where $-\lambda^2$ is an unknown constant. The time-dependent part is $$Q' + D\lambda^2 Q = 0$$

$$Q_\lambda(t) = e^{-D\lambda^2 t}.$$

At this point, rule out the trivial solution $\lambda=0$ as well as $\lambda^2<0$ or else the time part explodes. Therefore, $\lambda$ is real.

The spatial part is the radial part of the Helmholtz equation in spherical coordinates.

$$rP'' + 2P' + \lambda^2 rP = 0$$

$$(rP)'' + \lambda^2(rP) = 0$$

Temporarily define a new function S=rP:

$$S'' + \lambda^2 S = 0$$

$$S_\lambda = c_1 e^{\lambda ir} + c_2 e^{-\lambda ir}$$

Translating the boundary conditions on P to S:

At origin: $S(r=0)=0$

At boundary: $P(r=R)=0 \rightarrow S(r=R)=0$

Applying these boundary conditions gives $$S(0) = c_1 + c_2 = 0$$

$$c_1 = -c_2$$

And $$S(R) = c(e^{\lambda iR} - e^{-\lambda iR}) = 2ic\,\sin(\lambda R) = 0.$$

Here, we have used the trigonometric identity $$\sin(x) = \frac{e^{ix} - e^{-ix}}{2i}.$$

Since $\lambda>0$ the eigenvalues of the general solution are $$\lambda = \frac{n\pi}{R} \quad (n = 1, 2, 3, \dots )$$

The general solution is therefore given by $$c_g(r, t) = PQ = \frac{S}{r}Q = \sum_{n=1}^{\infty} c_n e^{-\lambda Dt}\frac{\sin(\lambda r)}{r}$$

To solve for the coefficients, it is helpful to notice that the spatial part can be re-written in terms of the first spherical Bessel function, $$j_0(x) = \frac{\sin(x)}{x}$$

(also known as sin c(x)). Any order of spherical Bessel functions form an orthonormal basis. Like the Fourier series, functions can be expanded in terms of a linear combination Bessel functions: this is called the Fourier-Bessel series. For the spherical Bessel functions, coefficients are given by $$c_n = \frac{\int_0^b f(r) j_\alpha\left(\frac{ur}{b}\right) r^2 dr}{\frac{1}{2}(bj_{\alpha+1}(u))^2}$$

Expand the function $f(r)=c_0$ in $j_0$:

$$c_n = \frac{\int_0^R c_0 j_0\left(\frac{n\pi}{R}r\right) r^2 dr}{\frac{1}{2}(Rj_1(n\pi))^2}$$

The second Bessel function is $$j_1(x) = \frac{\sin x}{x^2} - \frac{\cos x}{x}, \text{ so } (j_1(n\pi))^2 = \frac{1}{n^2\pi^2} = \frac{1}{R^2\lambda^2}.$$

$$c_n =$$

$$\frac{2\lambda^2}{R}\int_0^R r^2 f(r) j_0(\lambda r) dr = \frac{2c_0}{R}\int_0^R (\lambda r)^2\frac{\sin(\lambda r)}{\lambda r}dr = \frac{2c_0}{R}\int_0^R (\lambda r)\sin(\lambda r)dr$$

$$c_n = \frac{2c_0}{R}\left[\frac{\sin(\lambda r)}{\lambda} - r\cos(\lambda r)\right]_0^R$$

Note that $\sin \lambda R = \sin n\pi = 0$, while $\cos \lambda R = \cos n\pi = (-1)^n$. Finally, we are left with the satisfyingly simple result $$c_n = \frac{2c_0}{R}(-R(-1)^n) = 2c_0(-1)^{n+1}$$

Altogether, the Concentration Distribution within the Bead is Described by:

$$c(r, t) = 2c_0\sum_{n=1}^{\infty}(-1)^{n+1}e^{-\lambda^2 Dt}j_0(\lambda r), \lambda = \frac{n\pi}{R}.$$

Integrate over the volume to find the amount of remaining material over time:

$$M(t) = \int_V c(r, t)dV = 4\pi\int_0^R c(r, t)r^2 dr$$

-continued $$M(t) = 8\pi c_0 \sum_{n=1}^{\infty} \left[ (-1)^{n+1} e^{-\lambda^2 Dt} \int_0^R j_0(\lambda r) r^2 dt \right]$$

This integral is the same as the one encountered in the Fourier-Bessel projection above and is solved similarly.

$$I = \int_0^R r^2 j_0(\lambda r) dr = \frac{1}{\lambda^2} \int_0^R (\lambda r) \sin(\lambda r) dr$$

$$I = \frac{1}{\lambda^2}(-R(-1)^n) = \frac{R}{\lambda^2}(-1)^{n+1} = \frac{R^3}{n^2 \pi^2}(-1)^{n+1}$$

The Alternating Coefficient Cancels Out with the Previous One. Therefore, the Amount of Remaining Solute Over Time is Given by:

$$M(t) = \frac{8}{\pi} R^3 c_0 \sum_{n=1}^{\infty} \frac{1}{n^2} e^{-\lambda^2 Dt}, \lambda = \frac{n\pi}{R}$$

Note that when t=0 the sum simplifies to $$\sum \frac{1}{n^2} = \frac{\pi^2}{6},$$

assuring that $$M(t = 0) = \frac{4}{3}\pi R^3 c_0$$

as expected.

Figure 9A:
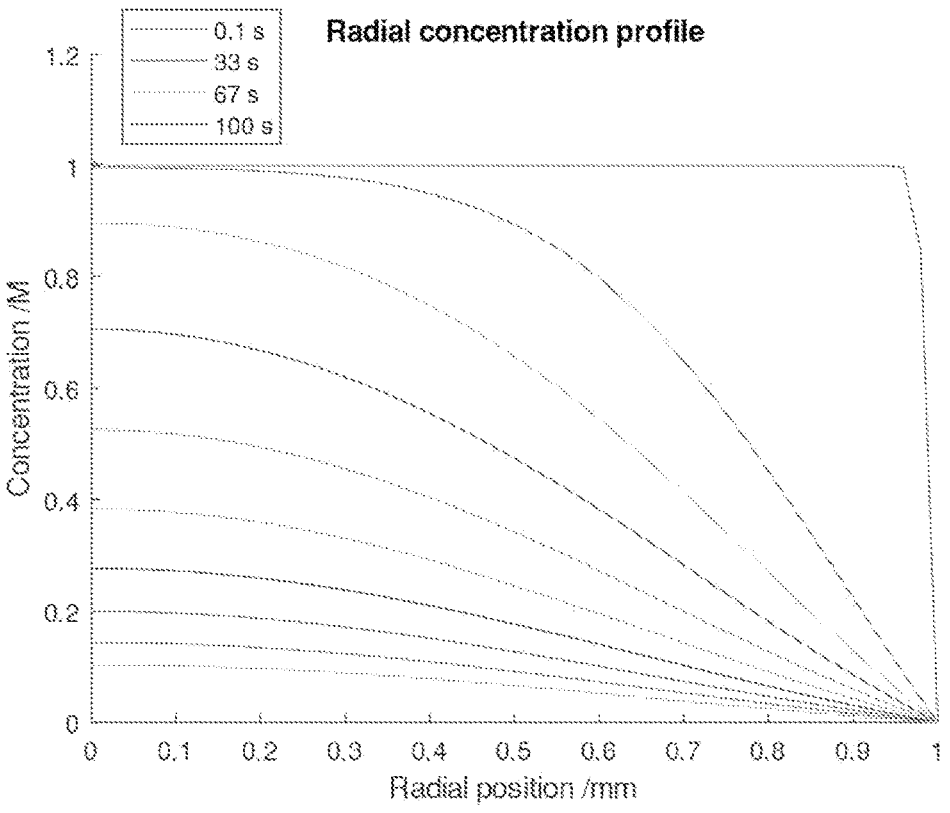
FIGS. 9A-9B are a pair of graphs of the radial concentration profile at different times (FIG. 9A) and rate of release (FIG. 9B), in accordance with the model of diffusion from an isolated bead with strong mixing described herein.
Figure 9B:
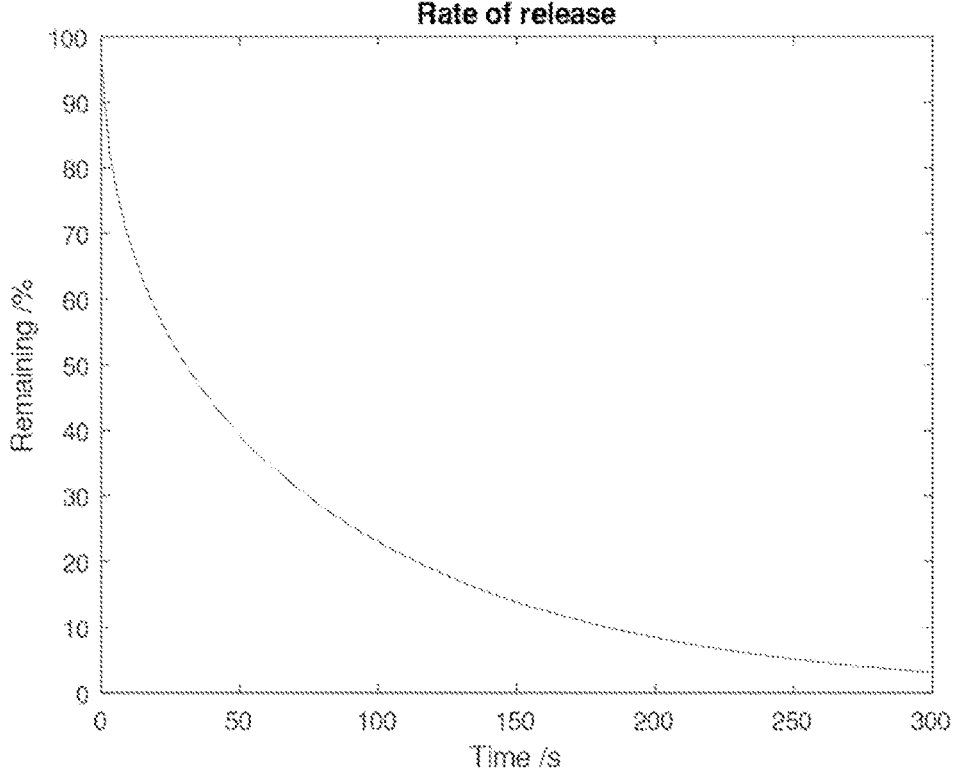

Here, we have plotted these functions for $c_0$=1M, R=1 mm and $$D = 1,000 \frac{\mu m^2}{s} = 10^{-5} \frac{cm^2}{s},$$

the approximate self-diffusion coefficient of water. FIG. 9A is the radial concentration profile at different times, from the center of the bead to the edge r=[0, R], and FIG. 9B is the rate of release.

Figure 10:
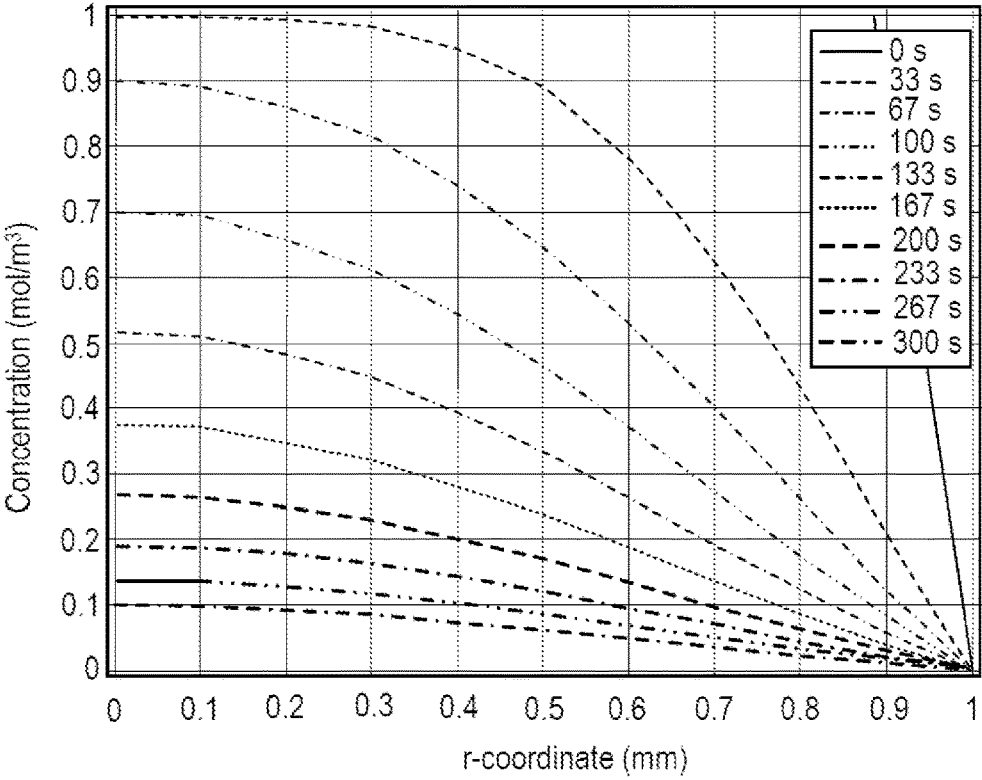
FIG. 10 is a graph of the radial concentration profile at different times calculated numerically using COMSOL, in accordance with the model of diffusion from an isolated bead with strong mixing described herein.

When we perform the same simulation numerically using COMSOL, we see identical results (FIG. 10).

The instantaneous rate of release at t=0 is technically infinite due to the discontinuity. This makes intuitive sense.

Figure 11:
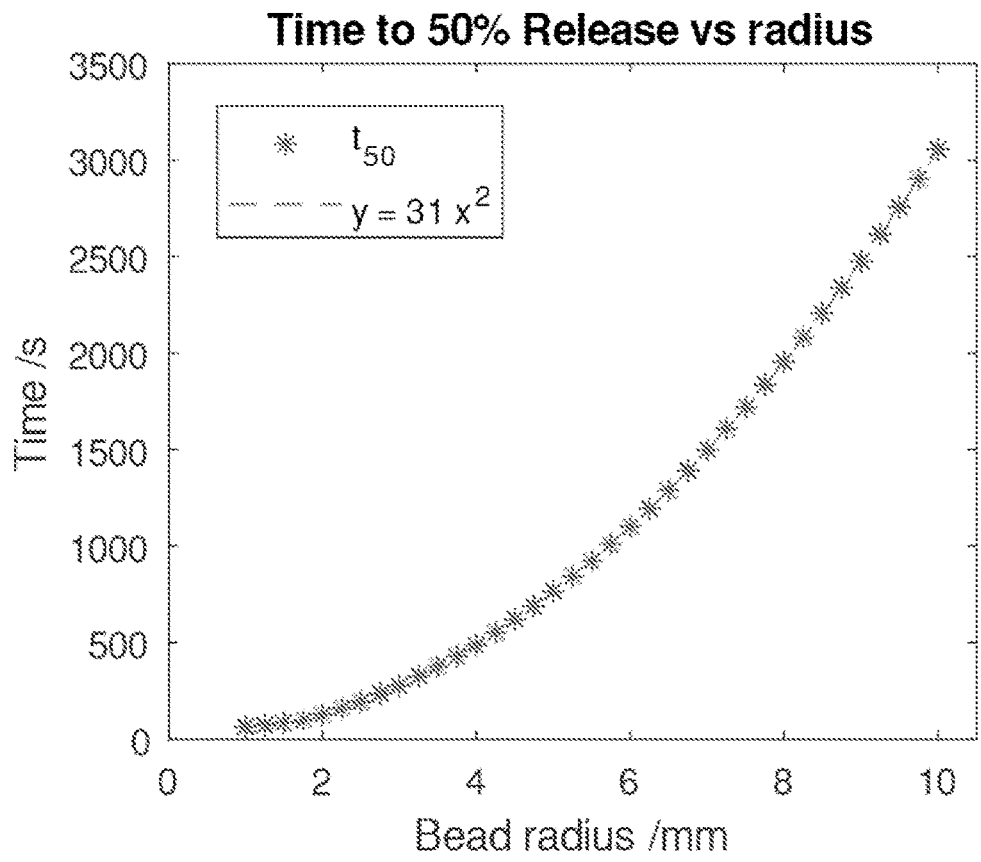
FIG. 11 is a graph of the time to 50% release versus bead radius, in accordance with the model of diffusion from an isolated bead with strong mixing described herein.

The canonical equilibration time constant for the system is is $\tau$=$R^2$/D, which is 1000 seconds with these parameters. At this time, less than one part in ten thousand remains in the bead, as even the slowest term of the expansion has decayed by 95%. However, this model is least useful at long time points. It is most useful at earlier time points, where the fixed boundary condition assumption is least inaccurate. We might also expect the rate of release at earlier time points to vary with the square of the radius. For example, consider the time to release 50% (FIG. 11). Indeed, it is also quadratic in this case.

5.2. Diffusion into a Finite Volume without Mixing

Figure 12:
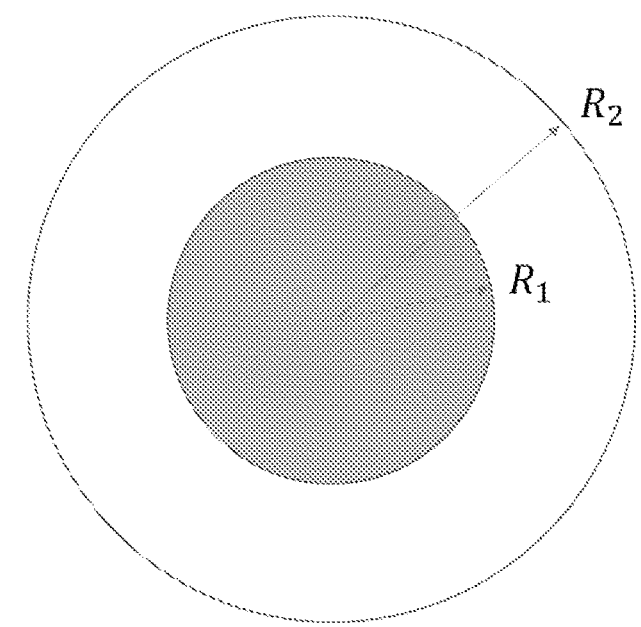
FIG. 12 is a schematic depiction of the model of diffusion into a finite volume without mixing in which a bead is centered within a spherical volume, where the bead radius is $R_1$ and the edge of the volume is $R_2$.

Now consider a second limiting case, in which many beads are suspended in a sort of lattice with no mixing. In contrast to the previous model, the exterior solute volume is limited and the concentration outside the bead will be allowed to increase. To simplify the system, we will describe a bead centered within a spherical volume, instead of a true lattice in $R^3$. The bead radius is $R_1$ and the edge of the volume is $R_2$ as shown in FIG. 12.

The general approach remains the same. The inner boundary condition at r=0 is the same, while the outer boundary condition has changed to the Neumann BC:

$$\frac{\partial c}{\partial t}\bigg|_{r=R_2} = 0$$

Translating this boundary condition to the temporary function S(r)=rP, as before:

$$S'|_{r=R_2} = ((rP)' + P)|_{r=R_2} = \frac{1}{R_2}S$$

$$c\lambda i(e^{\lambda i R_2} + e^{-\lambda i R_2}) = \frac{c}{R_2}(e^{\lambda i R_2} + e^{-\lambda i R_2})$$

$$\lambda R_2 \cos(\lambda R_2) - \sin(\lambda R_2) = 0.$$

The roots $\lambda$ which satisfy this condition are transcendental. It is therefore easier to proceed with numerical simulations.

We have simulated the rate of release from a bead with radius $R_1$=1 mm within a volume $R_2$=2 mm, such that the bead contains 12.5% of the total volume. As before, $c_0$=1M and $$D = 10^{-5}\frac{cm^2}{s}.$$

Figure 13A:
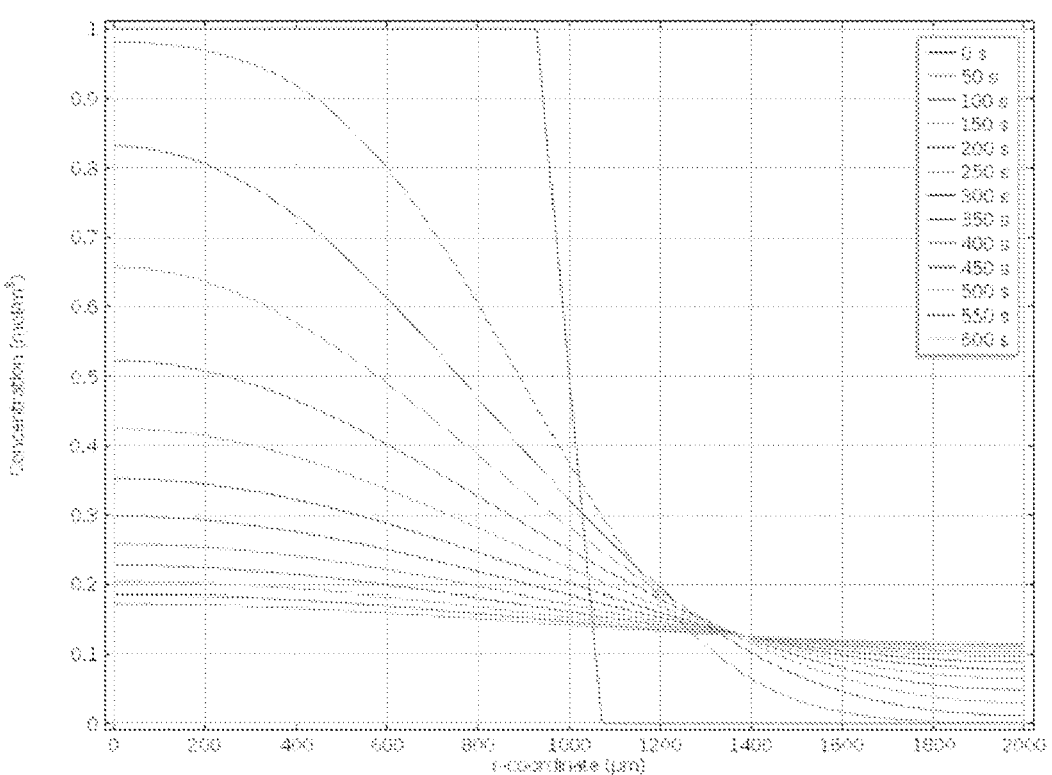
FIGS. 13A-13B are a pair of graphs of the radial plot of concentration (FIG. 13A) and the mean solute concentration outside the beads over time (FIG. 13B), in accordance with the model of diffusion into a finite volume without mixing described herein.
Figure 13B:
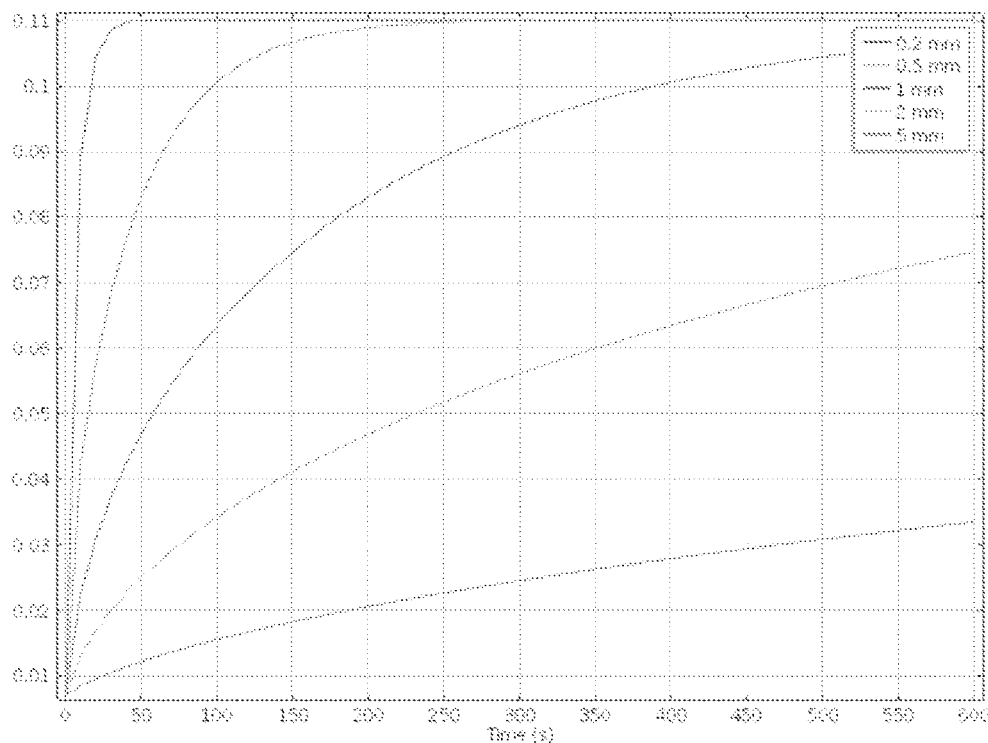

FIG. 13A is the radial plot of concentration, from the center of the bead to the edge of the boundary $R_2$. FIG. 13B is the mean solute concentration outside the beads over time.

Figure 14:
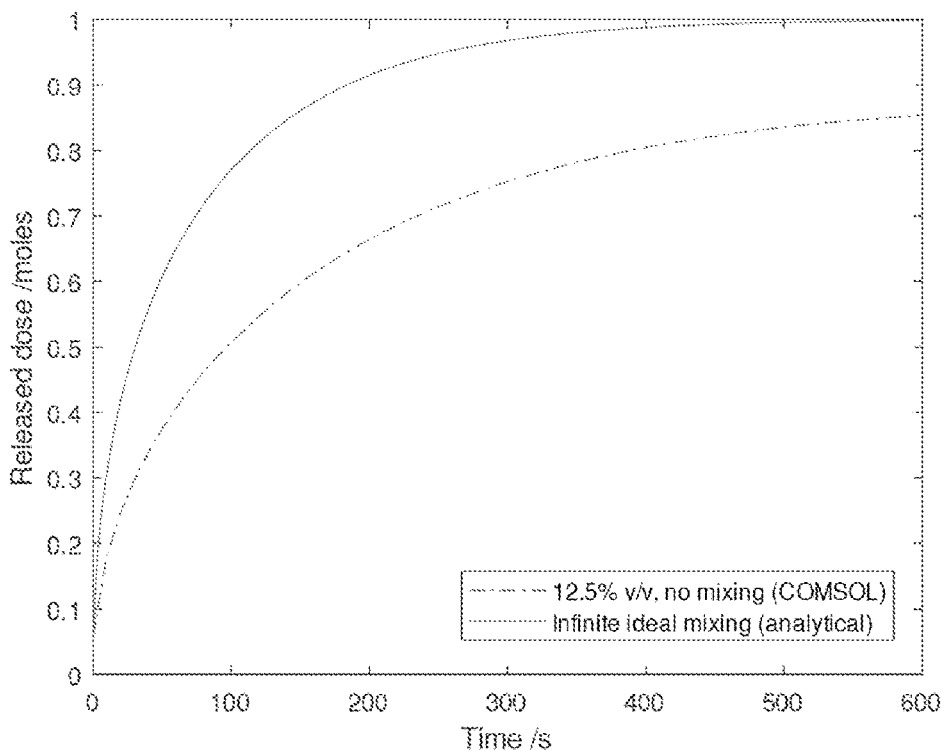
FIG. 14 is a graph comparing the total dose of released solute, in accordance with the model of diffusion with and without mixing described herein.

As expected, equilibrium is reached much slower than the previous case. We can compare the total dose of released solute in the two models. Together, these two curves represent the lower and upper bounds of the release rate which we would expect to measure in the presence of mixing. The release rates were plotted for beads with a diameter of 2 mm (FIG. 14).

5.3. Reversing the Problem: Diffusion into the Gel

All the solutions described previously are also valid for the reverse case, in which the solute is initially in the solution and not within the bead. The rate of diffusion of solute into the bead is precisely the same as previous scenarios reversed, with identical rate constants.

Figure 15:
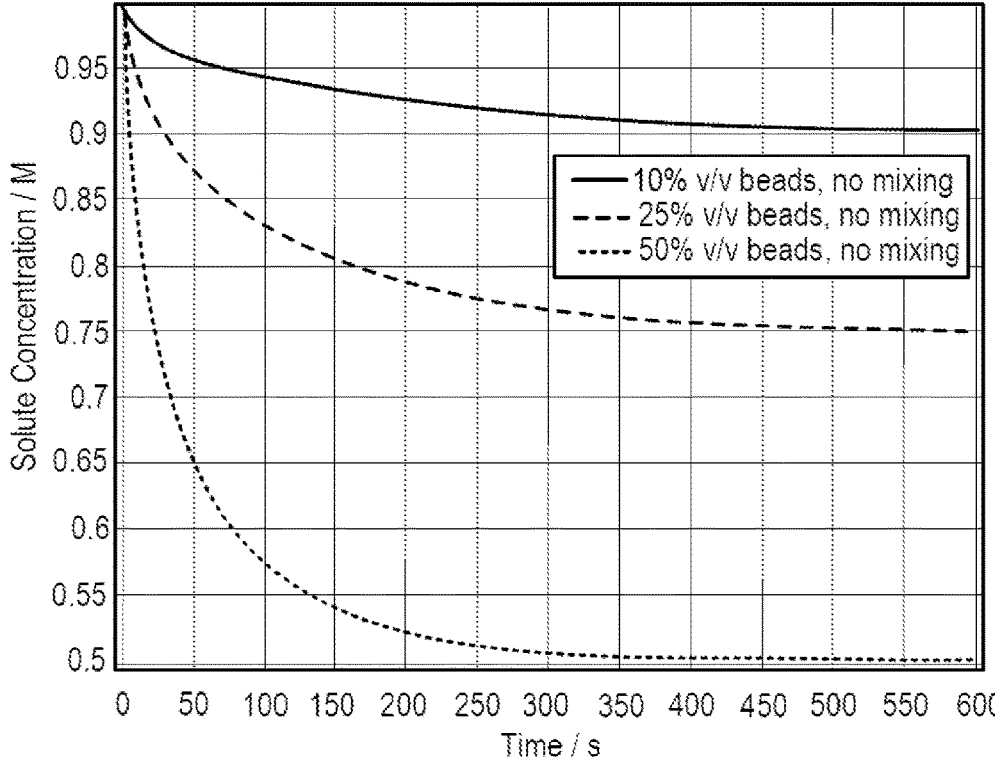
FIG. 15 is a graph showing solute concentration following the addition of differing amounts of beads (bead diameter=1 mm), in accordance with the model of diffusion without mixing described herein.

FIG. 15 shows the solute concentration following the addition of differing amounts of 1 mm beads. A larger volume fraction of bead removes larger amounts of solute, faster. This is due to extrinsic scaling: the equilibration time constants are the same.

Figure 16:
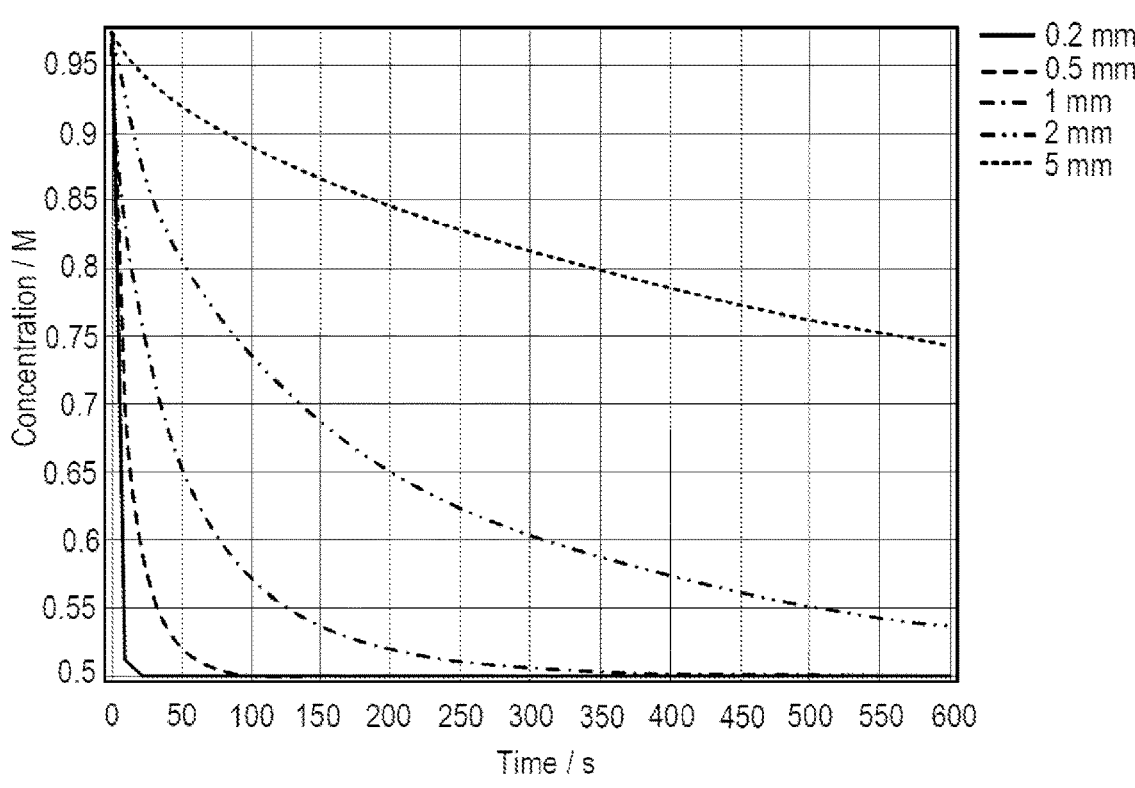
FIG. 16 is a graph showing solute concentration following the addition of differing bead sizes while keeping the final volume of beads the same as FIG. 15, in accordance with the model of diffusion without mixing described herein.

On the other hand, changing bead size while keeping the final volume fraction of beads the same results in different equilibration rates with the same equilibrium value (FIG. 16). The equilibration time constant scales with the square of the bead radius.

5.4. Bringing Convection into the Mix

The previous sections described the limiting behaviors of the system, as governed by diffusion alone. A more realistic model that includes convective mixing will help narrow down within this window. Perhaps the simplest way to do this is to return to the original 1-compartment model and adjust the outer boundary condition. Instead of assuming it is always strictly 0, we will assume it consists of a well-mixed compartment which contains all the released solute. For the case of solute release, the total starting amount or solute is $$m_0 = \frac{4}{3}\pi R^3 c_0.$$

Let's call the volume of this large, well-mixed exterior compartment Vex, and concentration within this compartment $c_{ex}$:

$$c(r = R, t) = c_{ex}(t) = \frac{\frac{4}{3}\pi R^3 c_0 - 4\pi \int_0^R c(r, t)r^2 dr}{V_{ex}}$$

Figure 17:
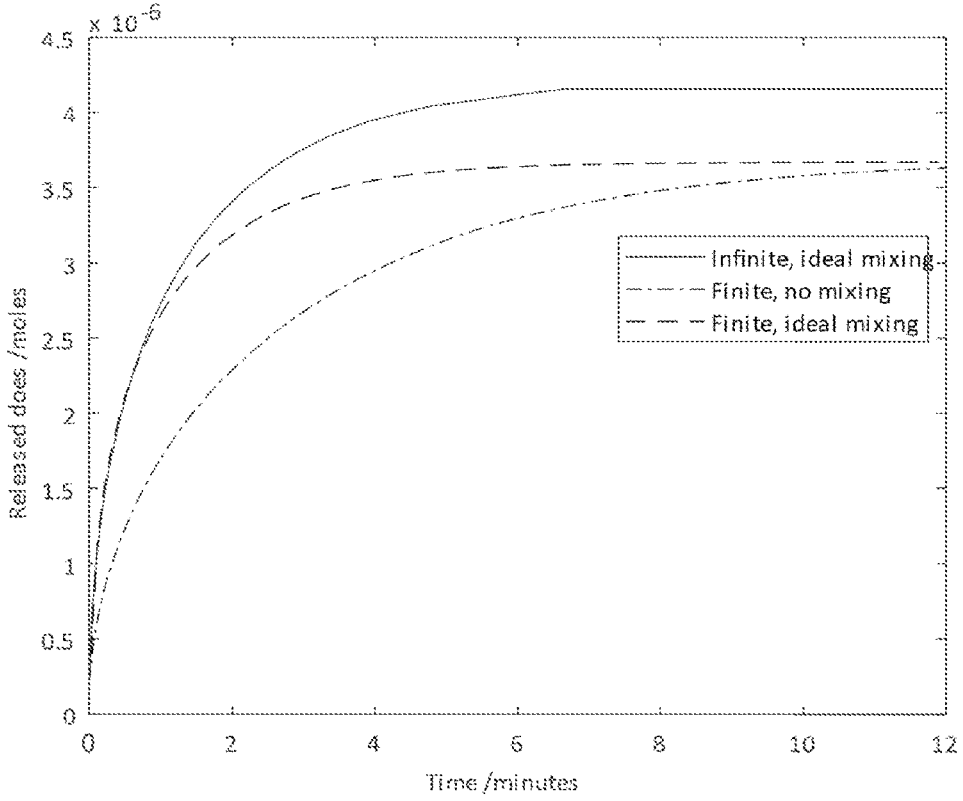
FIG. 17 is a graph showing release solute release rates, in accordance with the two-compartment model described herein.

This 'two-compartment' model is more accurate than the preceding two (see Section 5.1 and Section 5.2), and follows the limiting behavior that we would expect. Initially it is identical to the infinite well-mixed model. However, it reaches the same equilibrium value as the model with no mixing. The result is that equilibrium is reached faster than either of the two previous systems (FIG. 17).

Example 6: Synthesis of Hydrogel Beads

This Example describes the synthesis of calcium-alginate hydrogel beads.

First, the desired amount of beads and percent alginate is determined. For example, for 40 mL of 5% alginate beads, 2 g of alginic acid is added to 38 mL of water in a 50 mL falcon tube.

Next, the alginic acid in water is broken up into smaller pieces by vortexing. To dissolve the alginic acid into the water, place the falcon tube in a hot water bath (100-120 degrees ° C. with stirring at ~300 rpm) and vortex occasionally until the alginic acid is dissolved. Cool the homogenous alginate solution to room temperature, and de-gas using a vacuum chamber.

Figure 18:
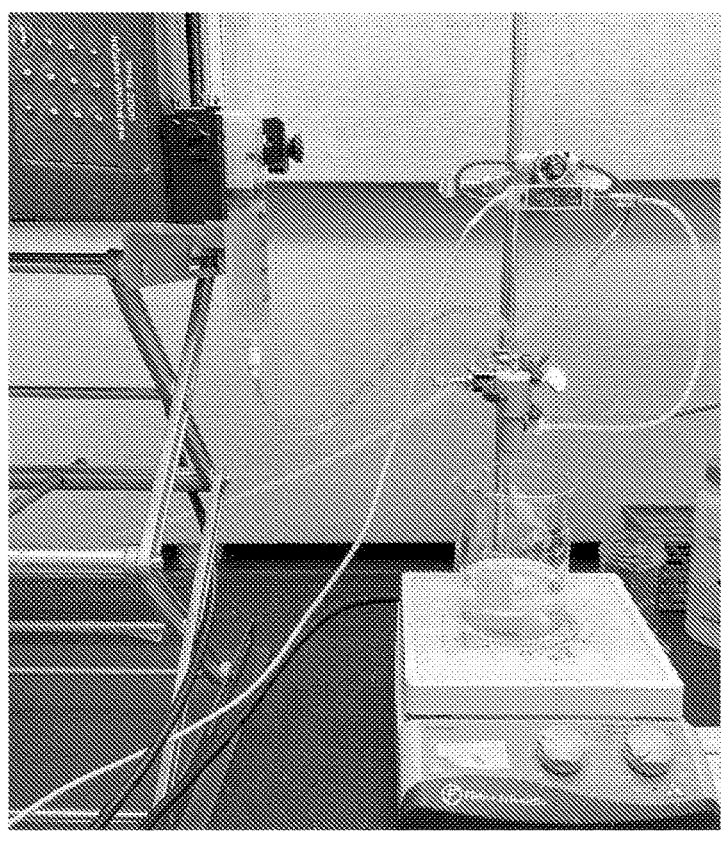
FIG. 18 is an image of an apparatus for preparing smaller beads using air flow.

To prepare small beads using air flow, set up a syringe/nozzle pump apparatus as shown in FIG. 18. Air flow changes bead size (e.g., set the air flow to ~4.00 L/min for small beads). Insert the syringe into the pump, and set the pump to have a refill rate of at least 5 mL/min and an infuse rate of 1 mL/min. The apparatus includes a bath of 4× the amount of desired beads of $CaCl_2$ (e.g., for making 50 mL beads, add ~200 mL of $CaCl_2$ to a 300 mL beaker) and a stand having a clamp for the nozzle, air flow reader/device, and hot plate at the base for the bath to sit upon. Fill the syringe with alginate. Attach a nozzle to the syringe and turn on air flow.

To start making the beads, stir the $CaCl_2$ solution on the hot plate. Set the pump to infuse mode and run the pump. While the alginate is flowing through the tube and has yet to reach the nozzle, the infuse rate is set to 5 mL/min. Lower the infuse rate to 1 mL/min before the gel reaches the nozzle.

Allow the beads to settle at the base of the beaker after it is removed from the hot plate. Decant the $CaCl_2$ solution and add fresh $CaCl_2$ (200 mM $CaCl_2$, 4× volume of beads). The washing step can be repeated. The hydrogel beads are ready for use or storage in fresh 200 mM $CaCl_2$ (4× volume of beads) at 4° C.

Figure 19:
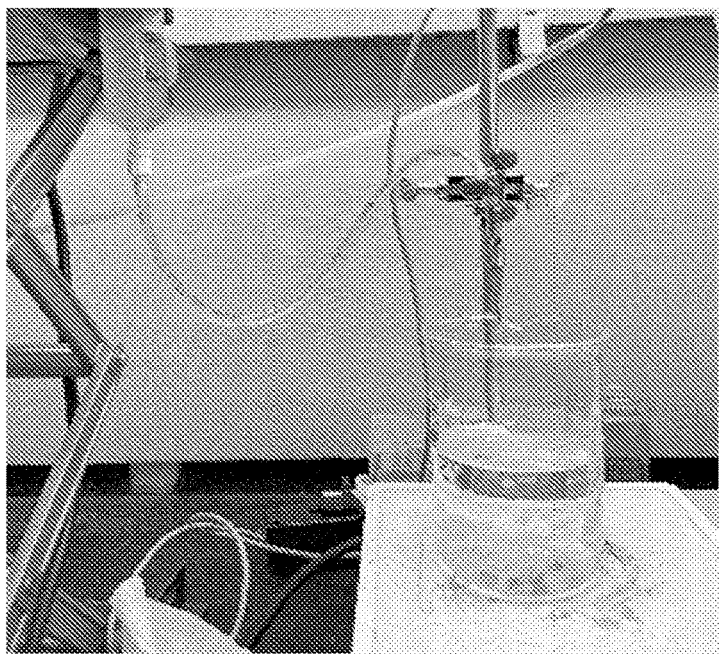
FIG. 19 is an image of an apparatus for preparing larger beads without using air flow.

To prepare larger beads without using air flow, the needle is attached directly to tubing as shown in FIG. 19. The distance from the tip of needle to the surface of the bath is 5 cm (this distance can change the size of the beads).

Fill the syringe with alginate, attach the open tubing to the syringe and stick the end into the falcon tube. Attach the needle to the end of the tubing to start the infuse process.

To start making larger beads, set the pump to infuse mode and hit run. Let the first few beads fall into the waste tube and then once gel is dropping at a consistent, regular pace, switch out the waste tube for the $CaCl_2$ bath. Keep the bath stirring throughout the bead making process at a rate fast enough so all the beads swirl around. Wash and store beads as described above for smaller beads.

REFERENCES

1. Stevanović S, Draper L M, Langhan M M, Campbell T E, Kwong M L, Wunderlich J R, et al. Complete Regression of Metastatic Cervical Cancer After Treatment With Human Papillomavirus—Targeted Tumor-Infiltrating T Cells. *J Clin Oncol* 2015; 33:1543-50.
2. June C H, O'Connor R S, Kawalekar O U, Ghassemi S, Milone M C. CAR T cell immunotherapy for human cancer. *Science* 2018; 359:1361-5.
3. Rosenberg S A, Restifo N P, Yang J C, Morgan R A, Dudley M E. Adoptive cell transfer: a clinical path to effective cancer immunotherapy. *Nature Reviews Cancer* 2008; 8:299-308.
4. Roberts Z J, Better M, Bot A, Roberts M R, Ribas A. Axicabtagene ciloleucel, a first-in-class CAR T cell therapy for aggressive NHL. *Leukemia & Lymphoma* 2018; 59:1785-96.
5. Holzinger A, Barden M, Abken H. The growing world of CAR T cell trials: a systematic review. *Cancer Immunol Immunother* 2016; 65:1433-50.
6. Sarnaik A, Khushalani N I, Chesney J A, Kluger H M, Curti B D, Lewis K D, et al. Safety and efficacy of cryopreserved autologous tumor infiltrating lymphocyte therapy (LN-144, lifileucel) in advanced metastatic melanoma patients who progressed on multiple prior therapies including anti-PD-1. *JCO* 2019; 37:2518-2518.
7. Dwarshuis N J, Parratt K, Santiago-Miranda A, Roy K. Cells as advanced therapeutics: State-of-the-art, challenges, and opportunities in large scale biomanufacturing of high-quality cells for adoptive immunotherapies. *Advanced Drug Delivery Reviews* 2017; 114:222-39.
8. Levine B L, Miskin J, Wonnacott K, Keir C. Global Manufacturing of CAR T Cell Therapy. *Molecular Therapy—Methods & Clinical Development* 2017; 4:92-101.
9. Künkele A, Taraseviciute A, Finn L S, Johnson A J, Berger C, Finney 0, et al. Preclinical Assessment of CD171-Directed CAR T-cell Adoptive Therapy for Childhood Neuroblastoma: CE7 Epitope Target Safety and Product Manufacturing Feasibility. *Clin Cancer Res* 2017; 23:466-77.
10. Schuster S J, Svoboda J, Chong E A, Nasta S D, Mato A R, Anak Ö, et al. Chimeric Antigen Receptor T Cells in Refractory B-Cell Lymphomas. *New England Journal of Medicine* 2017; 377:2545-54.

11. Lemieux J, Jobin C, Simard C, Néron S. A global look into human T cell subsets before and after cryopreservation using multiparametric flow cytometry and two-dimensional visualization analysis. *Journal of Immunological Methods* 2016; 434:73-82.

12. Costantini A, Mancini S, Giuliodoro S, Butini L, Regnery C M, Silvestri G, et al. Effects of cryopreservation on lymphocyte immunophenotype and function. *Journal of Immunological Methods* 2003; 278:145-55.

13. Golab K, Leveson-Gower D, Wang X-J, Grzanka J, Marek-Trzonkowska N, Krzystyniak A, et al. Challenges in cryopreservation of regulatory T cells (Tregs) for clinical therapeutic applications. *International Immunopharmacology* 2013; 16:371-5.

14. Beres A, Drobyski W. The Role of Regulatory T Cells in the Biology of Graft Versus Host Disease. *Front Immunol* 2013; 4.

15. Papadopoulou A, Gerdemann U, Katari U L, Tzannou I, Liu H, Martinez C, et al. Activity of Broad-Spectrum T Cells as Treatment for AdV, EBV, CMV, BKV, and HHV6 Infections after HSCT. *Science Translational Medicine* 2014; 6.

16. Esensten J H, Bluestone J A, Lim W A. Engineering Therapeutic T Cells: From Synthetic Biology to Clinical Trials. *Annual Review of Pathology*: Mechanisms of Disease 2017; 12:305-30.

17. Mock U, Nickolay L, Cheung G W-K, Zhan H, Peggs K, Johnston I C, et al. Automated Lentiviral Transduction of T Cells with Cars Using the Clinimacs Prodigy. *Blood* 2015; 126:2043-2043.

18. Hopewell E L, Cox C, Pilon-Thomas S, Kelley L L. Tumor-infiltrating lymphocytes: Streamlining a complex manufacturing process. *Cytotherapy* 2019; 21:307-14.

19. Fesnak A D, June C H, Levine B L. Engineered T cells: the promise and challenges of cancer immunotherapy. *Nature Reviews Cancer* 2016; 16:566-81.

20. Lipsitz Y Y, Milligan W D, Fitzpatrick I, Stalmeijer E, Farid S S, Tan K Y, et al. A roadmap for cost-of-goods planning to guide economic production of cell therapy products. *Cytotherapy* 2017; 19:1383-91.

21. Kvarnström M, Jenmalm M C, Ekerfelt C. Effect of cryopreservation on expression of Th1 and Th2 cytokines in blood mononuclear cells from patients with different cytokine profiles, analysed with three common assays: an overall decrease of interleukin-4. *Cryobiology* 2004; 49:157-68.

22. Cox M A, Kastrup J, Hrubiško M. Historical perspectives and the future of adverse reactions associated with haemopoietic stem cells cryopreserved with dimethyl sulfoxide. *Cell Tissue Bank* 2012; 13:203-15.

23. Cruz C R, Hanley P J, Liu H, Torrano V, Lin Y-F, Arce J A, et al. Adverse events following infusion of T cells for adoptive immunotherapy: a 10-year experience. *Cytotherapy* 2010; 12:743-9.

24. Atasseven E, Tüfekçi Ö, Yilmaz S, Güleryüz H, Ören H. Neurotoxicity Associated With Dimethyl Sulfoxide Used in Allogeneic Stem Cell Transplantation. *Journal of Pediatric Hematology/Oncology* 2017; 39:e297.

25. Windrum P, Morris T C M. Severe neurotoxicity because of dimethyl sulphoxide following peripheral blood stem cell transplantation. *Bone Marrow Transplantation* 2003; 31:315.

26. Windrum P, Morris T C M, Drake M B, Niederwieser D, Ruutu T. Variation in dimethyl sulfoxide use in stem cell transplantation: a survey of EBMT centres. *Bone Marrow Transplantation* 2005; 36:601-3.

27. Neelapu S S, Locke F L, Bartlett N L, Lekakis L J, Miklos D B, Jacobson C A, et al. Axicabtagene Ciloleucel CAR T-Cell Therapy in Refractory Large B-Cell Lymphoma. *New England Journal of Medicine* 2017; 377:2531-44.

28. Calmels B, Houzé P, Hengesse J-C, Ducrot T, Malenfant C, Chabannon C. Preclinical evaluation of an automated closed fluid management device: Cytomate T M, for washing out DMSO from hematopoietic stem cell grafts after thawing. *Bone Marrow Transplantation* 2003; 31:823.

29. Shu Z, Hughes S M, Fang C, Huang J, Fu B, Zhao G, et al. A study of the osmotic characteristics, water permeability, and cryoprotectant permeability of human vaginal immune cells. *Cryobiology* 2016; 72:93-9.

30. Best B P. Cryoprotectant Toxicity: Facts, Issues, and Questions. *Rejuvenation Res* 2015; 18:422-36.

31. Notman R, Noro M, O'Malley B, Anwar J. Molecular Basis for Dimethylsulfoxide (DMSO) Action on Lipid Membranes. *J Am Chem Soc* 2006; 128:13982-3.

32. Chetty S, Pagliuca F W, Honore C, Kweudjeu A, Rezania A, Melton D A. A simple tool to improve pluripotent stem cell differentiation. *Nature Methods* 2013; 10:553-6.

33. Pi C-H, Yu G, Petersen A, Hubel A. Characterizing the "sweet spot" for the preservation of a T-cell line using osmolytes. *Scientific Reports* 2018; 8:16223.

34. Kloverpris H, Fomsgaard A, Handley A, Ackland J, Sullivan M, Goulder P. Dimethyl sulfoxide (DMSO) exposure to human peripheral blood mononuclear cells (PBMCs) abolish T cell responses only in high concentrations and following coincubation for more than two hours. *Journal of Immunological Methods* 2010; 356:70-8.

35. Heo Y S, Lee H-J, Hassell B A, Irimia D, Toth T L, Elmoazzen H, et al. Controlled loading of cryoprotectants (CPAs) to oocyte with linear and complex CPA profiles on a microfluidic platform. *Lab Chip* 2011; 11:3530-7.

36. Zhou X, Yang Y, Zhang X. Microfluidic Device reduces Osmotic injury to Oocytes during loading and unloading cryoprotectants. Cryobiology 2018; 80:189-90.

37. Song Y S, Moon S, Hulli L, Hasan S K, Kayaalp E, Demirci U. Microfluidics for cryopreservation. *Lab Chip* 2009; 9:1874-81.

38. Krasemann L, Tieke B. Selective Ion Transport across Self-Assembled Alternating Multilayers of Cationic and Anionic Polyelectrolytes. *Langmuir* 2000; 16:287-90.

39. Zhao S, Caruso F, Dähne L, Decher G, De Geest B G, Fan J, et al. The Future of Layer-by-Layer Assembly: A Tribute to ACS Nano Associate Editor Helmuth Möhwald. *ACS Nano* 2019; 13:6151-69.

40. Chen L, An H Z, Doyle P S. Synthesis of Nonspherical Microcapsules through Controlled Polyelectrolyte Coating of Hydrogel Templates. *Langmuir* 2015; 31:9228-35.

41. Amsden B. Solute Diffusion within Hydrogels. Mechanisms and Models. *Macromolecules* 1998; 31:8382-95.

42. Tanaka H, Matsumura M, Veliky I A. Diffusion characteristics of substrates in Ca-alginate gel beads. *Biotechnology and Bioengineering* 1984; 26:53-8.

43. Zilionis R, Nainys J, Veres A, Savova V, Zemmour D, Klein A M, et al. Single-cell barcoding and sequencing using droplet microfluidics. *Nature Protocols* 2017; 12:44-73.

44. Bunker B C, Huber D L, Kent M S, Yim H, Curro J G, Lopez G P, et al. Switchable Hydrophobic-Hydrophilic Surfaces. 2002.

45. Zhang J, Peppas N A. Synthesis and Characterization of pH- and Temperature-Sensitive Poly(methacrylic acid)/Poly(N-isopropylacrylamide) Interpenetrating Polymeric Networks. *Macromolecules* 2000; 33:102-7.

46. Weng L, Ellett F, Edd J, K. Wong K H, Uygun K, Irimia D, et al. A highly-occupied, single-cell trapping microarray for determination of cell membrane permeability. *Lab on a Chip* 2017; 17:4077-88.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for cryopreservation of cells, the method comprising:
   (a) suspending the cells in an isotonic solution,
   (b) adding a plurality of hydrogel beads comprising one or more cryoprotective agents to the isotonic solution, wherein each hydrogel bead in the plurality of hydrogel beads has a diameter of 1 to 5 mm,
   (c) incubating the isotonic solution and the plurality of hydrogel beads for a time and under conditions sufficient to release the one or more cryoprotective agents from the plurality of hydrogel bead into the isotonic solution,
   (d) separating the cells from the plurality of hydrogel beads, and
   (e) cooling the cells to a temperature sufficient to cryopreserve the cells.

2. The method of claim 1, wherein each hydrogel bead in the plurality of hydrogel beads has a volume of 0.5 to 65 µL or a weight of 0.5 to 65 mg.

3. The method of claim 1, wherein the one or more cryoprotective agents are present in each hydrogel bead in the plurality of hydrogel beads at an amount of 2.5% to 50% (v/v).

4. The method of claim 1, wherein the one or more cryoprotective agents comprises an intracellular cryoprotective agent, an extracellular cryoprotective agent, or both.

5. The method of claim 4, wherein the intracellular cryopreservative agent is selected from the group consisting of glycerol, ethylene glycol, 1,2-propanediol, and dimethyl sulfoxide (DMSO).

6. The method of claim 4, wherein the extracellular cryoprotective agent is selected from the group consisting of sugars, dextran, polyvinyl pyrrolidone and hydroxyethyl starch.

7. The method of claim 1, wherein each hydrogel bead in the plurality of hydrogel beads comprises a biological polymer, a synthetic polymer, or a combination thereof.

8. The method of claim 1, wherein the isotonic solution is phosphate buffered saline (PBS) or cell culture media.

9. The method of claim 1, wherein the cells are plant cells, animal cells, bacterial cells, or fungal cells.

10. The method of claim 9, wherein the animal cells are mammalian cells.

11. The method of claim 1, wherein, in step (b), the amount of the isotonic solution by volume is 2 to 4 times greater than the amount of the plurality of hydrogel beads by weight.

12. The method of claim 1, wherein, in step (c), the cells and the plurality of hydrogel beads are incubated at room temperature.

13. The method of claim 1, wherein, in step (c), the cells and the plurality of hydrogel beads are incubated for 1 to 20 minutes.

14. The method of claim 1, wherein, in step (c), the cells and the plurality of hydrogel beads are incubated with mixing.

15. The method of claim 1, wherein, in step (d), separating the cells from the plurality of hydrogel beads comprises aspiration, filtration, centrifugation, or a combination thereof.

16. The method of claim 1, wherein the temperature sufficient to cryopreserve the cells is at or below −80° C.

17. A method for recovering cryopreserved cells in a cryopreservation solution comprising one or more cryoprotective agents, the method comprising:
   (a) thawing the cryopreserved cells in the cryopreservation solution at a temperature above freezing,
   (b) adding a plurality of hydrogel beads to the cryopreservation solution, wherein each hydrogel bead in the plurality of hydrogel beads has a diameter of 1 to 5 mm,
   (c) incubating the plurality of hydrogel beads and the cryopreservation solution for a time and under conditions sufficient for the plurality of hydrogel beads to absorb the one or more cryoprotective agents, and
   (d) separating the thawed cells from the plurality of hydrogel beads.

18. A method of preparing a plurality of hydrogel beads comprising one or more cryoprotective agents, the method comprising:
   (a) incubating a plurality of hydrogel beads and a cryoprotective solution comprising one or more cryoprotective agents for a time and under sufficient conditions for uptake of the one or more cryoprotective agents by the plurality of hydrogel beads, wherein each hydrogel bead in the plurality of hydrogel beads has a diameter of 1 to 5 mm, and
   (b) separating the plurality of hydrogel beads from the cryoprotective solution.

* * * * *